(12) United States Patent
Tsutsumi et al.

(10) Patent No.: US 10,268,164 B2
(45) Date of Patent: Apr. 23, 2019

(54) CIRCUIT DEVICE, PHYSICAL QUANTITY MEASUREMENT DEVICE, ELECTRONIC APPARATUS, AND VEHICLE

(71) Applicant: Seiko Epson Corporation, Tokyo (JP)

(72) Inventors: Akio Tsutsumi, Chino (JP); Takashi Kurashina, Matsumoto (JP); Katsuhiko Maki, Chino (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 15/901,044

(22) Filed: Feb. 21, 2018

(65) Prior Publication Data

US 2018/0239307 A1 Aug. 23, 2018

(30) Foreign Application Priority Data

Feb. 22, 2017 (JP) .................. 2017-030680

(51) Int. Cl.
| | | |
|---|---|---|
| *H03L 7/087* | (2006.01) | |
| *G04F 10/00* | (2006.01) | |
| *H03B 5/32* | (2006.01) | |
| *H03B 5/36* | (2006.01) | |
| *A61B 8/08* | (2006.01) | |
| *B60R 16/02* | (2006.01) | |
| *G01S 17/93* | (2006.01) | |
| *G01S 7/486* | (2006.01) | |
| *G01S 15/14* | (2006.01) | |

(52) U.S. Cl.
CPC ............. *G04F 10/005* (2013.01); *H03B 5/32* (2013.01); *H03B 5/362* (2013.01); *H03B 5/368* (2013.01); *H03L 7/087* (2013.01); *A61B 8/5207* (2013.01); *B60R 16/02* (2013.01); *G01S 7/4865* (2013.01); *G01S 15/14* (2013.01); *G01S 17/936* (2013.01)

(58) Field of Classification Search
CPC ......... G04F 10/005; H03B 5/32; H03L 7/087; G01S 17/936; A61B 8/5207; B60R 16/02
See application file for complete search history.

(56) References Cited

U.S. PATENT DOCUMENTS

2007/0085570 A1    4/2007  Matsuta
2009/0273384 A1   11/2009  Kojima et al.
(Continued)

FOREIGN PATENT DOCUMENTS

JP    H01-079687 A    3/1989
JP    H05-087954 A    4/1993
(Continued)

*Primary Examiner* — Kenneth B Wells
(74) *Attorney, Agent, or Firm* — Harness, Dickey & Pierce, P.L.C.

(57) ABSTRACT

A circuit device includes a first PLL circuit to which a first clock signal having a first clock frequency generated using a first resonator and a reference clock signal are input, and which performs phase synchronization between the first clock signal and the reference clock signal, a second PLL circuit to which a second clock signal generated using a second resonator and having a second clock frequency different from the first clock frequency and the reference clock signal are input, and which performs phase synchronization between the second clock signal and the reference clock signal, and a time-to-digital conversion circuit adapted to convert time into a digital value using the first clock signal and the second clock signal.

20 Claims, 21 Drawing Sheets

(56) References Cited

U.S. PATENT DOCUMENTS

2018/0091158 A1*  3/2018  Sudo ................... G04F 10/005
2018/0239307 A1*  8/2018  Tsutsumi ............. G04F 10/005

FOREIGN PATENT DOCUMENTS

| JP | 2007-110370 A | 4/2007 |
| JP | 2009-246484 A | 10/2009 |
| JP | 2010-119077 A | 5/2010 |

* cited by examiner

| fr (MHz) | f1 (MHz) | f2 (MHz) | N2 | M2 | N1 | M1 | $\Delta t = \|1/f1 - 1/f2\|$ (ps) |
|---|---|---|---|---|---|---|---|
| 101 | 102.01 | 102 | 102 | 101 | 101 | 100 | 0.96 |
| 102 | 189.04 | 189 | 63 | 34 | 139 | 75 | 1.12 |
| 201 | 276.04 | 276 | 92 | 67 | 103 | 75 | 0.53 |

FIG. 9

CIRCUIT DEVICE, PHYSICAL QUANTITY MEASUREMENT DEVICE, ELECTRONIC APPARATUS, AND VEHICLE

BACKGROUND

1. Technical Field

The present invention relates to a circuit device, a physical quantity measurement device, an electronic apparatus, a vehicle, and so on.

2. Related Art

In the past, there has been known a circuit device having a time-to-digital conversion circuit. The time-to-digital conversion circuit converts time into a digital value. As related art examples of a circuit device having such a time-to-digital conversion circuit, there are known related art technologies disclosed in, for example, JP-A-2009-246484 (Document 1), JP-A-2007-110370 (Document 2), JP-A-2010-119077 (Document 3) and JP-A-5-87954 (Document 4).

In the related art technologies of Documents 1 through 3, the time-to-digital conversion is realized using a so-called vernier delay circuit. In the vernier delay circuit, the time-to-digital conversion is realized using delay elements as semiconductor elements.

In Document 4, there is disclosed a minute time measurement device provided with a first quartz crystal oscillator for outputting a first pulse, a second quartz crystal oscillator for outputting a second clock pulse, an edge matching detection circuit, a synchronous counter, a microcomputer, and a transmission time control section. The edge matching detection circuit detects a synchronization point between the first and second clock pulses. The synchronous counter performs a counting process in sync with the first and second clock pulses. The microcomputer calculates the unknown time from a start pulse to a stop pulse based on the value of the synchronous counter. The transmission time control section outputs the start pulse in accordance with the output of the edge matching circuit, and the values of the synchronous counter and the microcomputer.

In the related art technology of Document 4, the edge matching detection circuit detects the synchronization point where the falling edges of the first and second clock pulses coincide with each other. Then, the synchronous counter starts the counting process in sync with the first and second clock pulses in the case in which the synchronization point is detected, and then performs the time measurement for calculating the unknown time from the start pulse to the stop pulse based on the result of the counting process.

However, in this related art technology, since the time measurement cannot be started unless the synchronization point is detected, the conversion time of the time-to-digital conversion increases. Further, in the case in which the relationship in clock frequency between the first and second clock pulses is in the frequency relationship in which the edges fail to coincide with each other at the synchronization point, it is difficult to realize the time-to-digital conversion. Further, since the timing to be the reference of the process of the time-to-digital conversion cannot appropriately be set, the process of the time-to-digital conversion becomes complicated. Further, if an error exists in the matching detection of the edges of the clock pulses at the synchronization point, the accuracy of the time-to-digital conversion deteriorates.

SUMMARY

According to some aspects of the invention, it is possible to provide a circuit device, a physical quantity measurement device, an electronic apparatus, a vehicle and so on capable of improving the performance and simplification of the process of the time-to-digital conversion.

The invention can be implemented as the following forms or embodiments.

An aspect of the invention relates to a circuit device including a first PLL circuit that receives a first clock signal having a first clock frequency generated by a first resonator and a reference clock signal, and performs phase synchronization between the first clock signal and the reference clock signal, a second PLL circuit that receives a second clock signal generated by a second resonator and having a second clock frequency different from the first clock frequency and the reference clock signal, and performs phase synchronization between the second clock signal and the reference clock signal, and a time-to-digital conversion circuit adapted to convert time into a digital value using the first clock signal and the second clock signal.

According to this aspect of the invention, the phase synchronization between the first clock signal and the reference clock signal is performed by the first PLL circuit, and the phase synchronization between the second clock signal and the reference clock signal is performed by the second PLL circuit. Thus, the phase synchronization between the first and second clock signals is realized. In this case, by performing the phase synchronization using the first and second PLL circuits, it becomes possible to increase the frequency of the phase synchronization compared to the case of performing the phase synchronization between the first and second clock signals using a single PLL circuit. Further, the time-to-digital conversion circuit performs the time-to-digital conversion of conversing time into a digital value using the first and second clock signals having the first and second clock frequencies synchronized in phase with each other in such a manner. By adopting this configuration, it becomes possible to realize the improvement in performance and the simplification of the time-to-digital conversion process using the first and second clock signals.

In the aspect of the invention, the reference clock signal may be a clock signal generated using a third resonator.

With this configuration, by generating the reference clock signal using the third resonator, further improvement in accuracy of the time-to-digital conversion can be achieved.

In the aspect of the invention, the time-to-digital conversion circuit may convert the time into the digital value with the resolution corresponding to a frequency difference between the first clock frequency and the second clock frequency.

With this configuration, it becomes possible to set the resolution of the time-to-digital conversion using the frequency difference between the first and second clock frequencies, and the improvement in performance of the time-to-digital conversion can be realized.

In the aspect of the invention, defining the first clock frequency as f1 and the second clock frequency as f2, the time-to-digital conversion circuit may convert the time into the digital value with the resolution $\Delta t$ expressed as $$\Delta t = |f1-f2|/(f1 \times f2).$$

With this configuration, it becomes possible to make the resolution finer by, for example, decreasing the frequency difference between the first and second clock frequencies, and setting the first and second clock frequencies to higher frequencies, and it is possible to realize the improvement in performance of the time-to-digital conversion.

In the aspect of the invention, in the case of defining the first clock frequency as f1, the second clock frequency as f2, and a clock frequency of the reference clock signal as fr, the first PLL circuit may perform the phase synchronization between the first clock signal and the reference clock signal so as to fulfill N1/f1=M1/fr (N1 and M1 are each no smaller than 2, and are different from each other), and the second PLL circuit may perform the phase synchronization between the second clock signal and the reference clock signal so as to fulfill N2/f2=M2/fr (N2 and M2 are each no smaller than 2, and are different from each other).

With this configuration, the phase synchronization at appropriate phase synchronization timing becomes possible, and it becomes possible to achieve the improvement in performance and the simplification of the time-to-digital conversion process.

In the aspect of the invention, N1, M1, N2, and M2 may be set so that the relationship of |N1×M2−N2×M1|=1 is true.

With this configuration, the first clock signal and the second clock signal become to be shifted as much as, for example, one clock cycle in, for example, every phase synchronization period, and it becomes possible to achieve simplification of the process of the time-to-digital conversion, and so on.

In the aspect of the invention, in a case of defining the resolution of the time-to-digital conversion as Δt, and N and M as N=N1×M2, M=N2×M1, the phase synchronization between the first clock signal and the second clock signal may be performed by the first PLL circuit and the second PLL circuit so as to fulfill the following expression.

$$\Delta t = |N-M|/(N \times f2) = |N-M|/(M \times f1)$$

With this configuration, it becomes possible to set N=N1×M2, M=N2×M1 in accordance with the resolution Δt required for the time-to-digital conversion to achieve the phase synchronization between the first and second clock signals.

In the aspect of the invention, the first PLL circuit may include a first phase detector adapted to perform phase comparison between one of the first clock signal and a signal based on the first clock signal, and one of the reference clock signal and a signal based on the reference clock signal, and the second PLL circuit may include a second phase detector adapted to perform phase comparison between one of the second clock signal and a signal based on the second clock signal, and one of the reference clock signal and a signal based on the reference clock signal.

With this configuration, it becomes possible to realize the phase synchronization between the first and second clock signals due to the feedback control of the phase comparison result performed in the first and second phase detectors.

In the aspect of the invention, the first PLL circuit may include a first frequency divider circuit adapted to divide the frequency of the first clock signal to obtain a first frequency-divided clock signal, and output the first frequency-divided clock signal to the first phase detector as the signal based on the first clock signal, and a second frequency divider circuit adapted to divide the frequency of the reference clock signal to obtain a second frequency-divided clock signal, and output the second frequency-divided clock signal to the first phase detector as the signal based on the reference clock signal, and the second PLL circuit may include a third frequency divider circuit adapted to divide the frequency of the second clock signal to obtain a third frequency-divided clock signal, and output the third frequency-divided clock signal to the second phase detector as the signal based on the second clock signal, and a fourth frequency divider circuit adapted to divide the frequency of the reference clock signal to obtain a fourth frequency-divided clock signal, and output the fourth frequency-divided clock signal to the second phase detector as the signal based on the reference clock signal.

By providing the first and second frequency divider circuits and the third and fourth frequency divider circuits, it becomes possible to perform the feedback control of the phase comparison result between the first and second frequency-divided clock signals in the first phase detector and the feedback control of the phase comparison result between the third and fourth frequency-divided clock signals in the second phase detector to realize the phase synchronization between the first and second clock signals.

In the aspect of the invention, in a case of defining the first clock frequency as f1, the second clock frequency as f2, and a frequency of the reference clock signal as fr, the first frequency divider circuit may divide the frequency of the first clock signal and the second frequency divider circuit may divide the frequency of the reference clock signal so as to fulfill N1/f1=M1/fr (N1 and M1 are each no smaller than 2, and are different from each other), and the third frequency divider circuit may divide the frequency of the second clock signal and the fourth frequency divider circuit may divide the frequency of the reference clock signal so as to fulfill N2/f2=M2/fr (N2 and M2 are each no smaller than 2, and are different from each other).

With this configuration, the phase synchronization at appropriate phase synchronization timing becomes possible, and it becomes possible to achieve the improvement in performance and the simplification of the time-to-digital conversion process.

In the aspect of the invention, to the circuit device may include a first oscillation circuit controlled based on a phase comparison result of the first phase detector, and adapted to oscillate the first resonator to generate the first clock signal, and a second oscillation circuit controlled based on a phase comparison result of the second phase detector, and adapted to oscillate the second resonator to generate the second clock signal.

With this configuration, it becomes possible to realize the phase synchronization between the first and second clock signals by adjusting, for example, the first and second clock frequencies of the first and second clock signals, respectively, based on the phase detection result in the first and second phase detectors.

In the aspect of the invention, the circuit device may include a third oscillation circuit adapted to oscillate the third resonator to generate the reference clock signal.

With this configuration, the reference clock signal also becomes to be generated using the third resonator, and further improvement in accuracy of the time-to-digital conversion can be achieved.

In the aspect of the invention, the time-to-digital conversion circuit may convert a time difference in transition timing between a first signal and a second signal into a digital value.

With this configuration, it becomes possible to convert the time difference in transition timing between the first and second signal with high accuracy using the first and second clock signals generated by the first and second oscillators.

Another aspect of the invention relates to a physical quantity measurement device including any one of the circuit devices described above, the first resonator adapted to generate the first clock signal, and the second resonator adapted to generate the second clock signal.

By performing the time-to-digital conversion using the first and second oscillators as described above, the measurement process of the physical quantity higher inaccuracy becomes possible.

Still another aspect of the invention relates to an electronic apparatus including any one of the circuit devices described above.

Still another aspect of the invention relates to a vehicle including any one of the circuit devices described above.

BRIEF DESCRIPTION OF THE DRAWINGS

The invention will be described with reference to the accompanying drawings, wherein like numbers reference like elements.

FIG. 9 is a diagram showing an example of setting of a frequency division ratio.

DESCRIPTION OF AN EXEMPLARY EMBODIMENT

A preferred embodiment of the invention will hereinafter be described in detail. It should be noted that the embodiment described hereinafter does not unreasonably limit the content of the invention as set forth in the appended claims, and all of the constituents described in the embodiment are not necessarily essential as the elements for solving the problem of the invention.

1. Circuit Device

Figure 1:
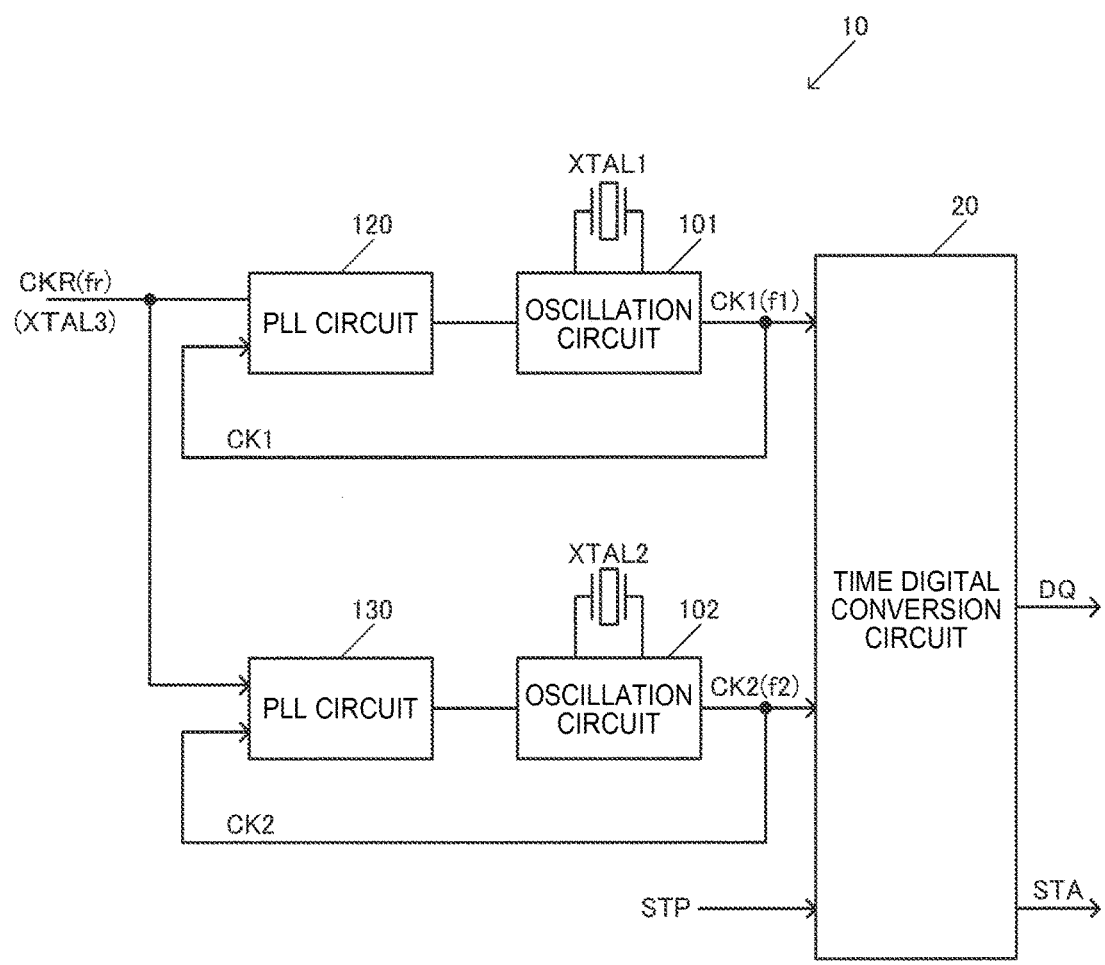
FIG. 1 is a diagram showing a configuration example of a circuit device according to an embodiment of the invention.

FIG. 1 shows a configuration example of a circuit device 10 according to the present embodiment. The circuit device 10 includes a time-to-digital conversion circuit 20, and PLL circuits 120, 130 (first and second PLL circuits; a synchronization circuit). Further, the circuit device 10 can include oscillation circuits 101, 102 (first and second oscillation circuits). It should be noted that the configuration of the circuit device 10 is not limited to the configuration shown in FIG. 1, but a variety of practical modifications such as elimination of some of the constituents (e.g., the oscillation circuits) or addition of other constituents are possible.

The time-to-digital conversion circuit 20 converts time into a digital value using a clock signal CK1 and a clock signal CK2. Specifically, to the time-to-digital conversion circuit 20, there are input a clock signal CK1 (a first clock signal) with a clock frequency f1 (a first clock frequency) and a clock signal CK2 (a second clock signal) with a clock frequency f2 (a second clock frequency), and the time-to-digital conversion circuit 20 converts the time into a digital value using these clock signals CK1, CK2. In the example shown in FIG. 1, the time-to-digital conversion circuit 20 converts the time difference in transition timing between a signal STA (a first signal, e.g., a start signal) and a signal STP (a second signal, e.g., a stop signal) into the digital value DQ using the clock signals CK1, CK2 with the clock frequencies f1, f2. It should be noted that although there is hereinafter described mainly the case of applying the method of the present embodiment to the time-to-digital conversion of converting the time difference in transition timing between the signals STA, STP (the first and second signals) into the digital value, the present embodiment is not limited to this case. For example, it is also possible to apply the method of the present embodiment to the time-to-digital conversion for measuring, for example, absolute time, and so on.

The clock frequency f2 is a frequency different from the clock frequency f1, and is, for example, a frequency lower than the clock frequency f1. Further, the time difference in transition timing between the signal STA and the signal STP is the time difference between the edges (e.g., between the rising edges, or between the falling edges) of the signal STA and the signal STP. Further, it is also possible for the time-to-digital conversion circuit 20 to perform a filter process (a digital filter process, a low-pass filter process) of the digital value DQ, and output the digital value DQ on which the filter process has been performed.

The PLL circuit 120 (the first PLL circuit) performs phase synchronization between the clock signal CK1 and a reference clock signal CKR. Specifically, the clock signal CK1 with the clock frequency f1 generated using a resonator XTAL1 (a first resonator) and the reference clock signal CKR are input to the PLL circuit 120, and the PLL circuit 120 performs the phase synchronization between the clock signal CK1 and the reference clock signal CKR. For example, the PLL circuit 120 phase-synchronizes the clock signal CK1 and the reference clock signal CKR with each other at every first phase synchronization timing (every first period). Specifically, the PLL circuit 120 performs the phase synchronization for making the transition timings of the clock signal CK1 and the reference clock CKR coincide with each other at every first phase synchronization timing.

Here, the clock frequency of the reference clock signal CKR is fr. The clock frequency fr is, for example, a frequency different from the clock frequencies f1, f2 of the clock signals CK1, CK2, and is, for example, a frequency lower than the clock frequencies f1, f2.

The PLL circuit 130 (the second PLL circuit) performs phase synchronization between the clock signal CK2 and the reference clock signal CKR. Specifically, the clock signal CK2 with the clock frequency f2 generated using a resonator XTAL2 (a second resonator) and the reference clock signal CKR are input to the PLL circuit 130, and the PLL circuit 130 performs the phase synchronization between the clock signal CK2 and the reference clock signal CKR. For example, the PLL circuit 130 phase-synchronizes the clock signal CK2 and the reference clock signal CKR with each other at every second phase synchronization timing (every second period). Specifically, the PLL circuit 130 performs the phase synchronization for making the transition timings of the clock signal CK2 and the reference clock CKR coincide with each other at every second phase synchronization timing.

As described above, in the present embodiment, the clock signal CK1 and the reference clock signal CKR are phase-synchronized with each other by the PLL circuit 120, and the clock signal CK2 and the reference clock signal CKR are phase-synchronized with each other by the PLL circuit 130. Thus, the phase synchronization between the clock signal CK1 and the clock signal CK2 is achieved. In other words, due to the PLL circuits 120, 130, the phase synchronization between the clock signals CK1, CK2 is achieved at every phase synchronization timing, and matching in the transition timing between the clock signals CK1, CK2 is achieved at every phase synchronization timing. It should be noted that it is also possible to adopt modified implementation of providing three or more PLL circuits (three or more resonators) to perform the phase synchronization between the clock signals CK1, CK2.

The reference clock signal CKR is a clock signal generated using, for example, a resonator XTAL3 (a third resonator). The reference clock signal CKR is a clock signal generated by oscillating, for example, the resonator XTAL3 with an oscillation circuit (a third oscillation circuit). By generating the reference clock signal CKR using the resonator XTAL3 oscillated by the oscillation circuit of, for example, the circuit device 10 in such a manner, it becomes possible to achieve the phase synchronization between the reference clock signal CKR and each of the clock signals CK1, CK2 using the reference clock signal CKR low in, for example, jitter and phase noise. Therefore, it becomes possible to achieve appropriate phase synchronization between the clock signals CK1, CK2, and it is possible to minimize the error caused by the time difference in transition timing between the clock signals CK1, CK2 at, for example, the phase synchronization timing. It should be noted that it is also possible to use an external clock signal or the like input from the outside of the circuit device 10 as the reference clock signal CKR.

After the phase synchronization timing between the clock signals CK1, CK2, the time-to-digital conversion circuit 20 makes the transition of the signal level of the signal STA based on the clock signal CK1. For example, the phase synchronization between the clock signals CK1, CK2 by the PLL circuits 120, 130 is performed, and after this phase synchronization timing, the time-to-digital conversion circuit 20 makes the transition of the signal level of the signal STA using the clock signal CK1. For example, the time-to-digital conversion circuit 20 makes the transition of the signal level of the signal STA from the first voltage level (e.g., an L level) to a second voltage level (e.g., an H level). Specifically, the time-to-digital conversion circuit 20 generates the signal STA as a pulse signal.

Then, the time-to-digital conversion circuit 20 performs the phase comparison between the signal STP, which makes the transition in the signal level in accordance with the signal STA, and the clock signal CK2 to thereby obtain the digital value DQ corresponding to the time difference. For example, due to the phase comparison, the time-to-digital conversion circuit 20 determines the timing, at which the anteroposterior relationship in the phase between the signal STP and the clock signal CK2 is reversed, to obtain the digital value DQ. The timing, at which the anteroposterior relationship in the phase is reversed, is the timing, at which the state, in which one of the signal STP and the clock signal CK2 lags in phase behind the other, is switched to the state, in which the one of the signals leads in phase over the other. The phase comparison between the signal STP and the clock signal CK2 can be realized by, for example, sampling one of the signal STP and the clock signal CK2 based on the other.

As described above, in the present embodiment, the phase synchronization between the clock signals CK1, CK2 is performed by the PLL circuits 120, 130, and after the timing of the phase synchronization, the signal STA is generated based on the clock signal CK1. Then, the phase comparison between the signal STP, the signal level of which makes the transition in accordance with the signal STA thus generated, and the clock signal CK2 is performed to thereby obtain the digital value DQ corresponding to the time difference in transition timing between the signal STA and the signal STP. By adopting this process, it becomes possible to realize the high-performance (high-accuracy, high-resolution) time-to-digital conversion while autonomously generating the first signal to be used for the time-to-digital conversion.

Further, in the present embodiment, by providing the PLL circuits 120, 130 to the circuit device 10, it becomes possible to match the transition timings of the clock signals CK1, CK2 with each other at every phase synchronization timing. Therefore, since it becomes possible to start the circuit processing using the phase synchronization timing as the reference timing, simplification of the circuit processing and the circuit configuration can be achieved. Further, it becomes possible to start the process of the time-to-digital conversion immediately after the phase synchronization timing due to the PLL circuits 120, 130 without waiting for the incidental matching of the transition timings of the clock signals CK1, CK2. Therefore, speeding-up of the time-to-digital conversion can be achieved. Further, by providing the PLL circuits 120, 130, the error caused by the time difference in transition timing between the clock signals CK1, CK2 at the phase synchronization timing can be minimized. Therefore, it becomes possible to achieve an increase in accuracy by sufficiently reducing the error, which is generated in a systematic manner due to the time difference.

For example, in the related art method of Document 4 described above, the matching of the edges of the first and second clock pulses is detected by the edge matching detection circuit, and the time measurement is started subject to the fact that the matching of the edges has been detected. However, according to the related art method, since the time measurement cannot be started unless matching of the edges of the first and second clock pulses is detected, there is a first problem that the start of the time measurement is delayed to increase the conversion time of the time-to-digital conversion. Further, in the case in which the relationship in clock frequency between the first and second clock pulses is in the frequency relationship in which the edges fail to match each other at the synchronization point, there is a second problem that the edges can only match each other by chance, and it becomes difficult to realize the time-to-digital conversion. Further, since the timing of the synchronization point of the first and second clock pulses cannot be decided in a systematic manner, there is a third problem that the circuit processing and the circuit configuration become complicated. Further, in the case in which an error exists in the matching detection of the edges of the first and second clock pulses, there is a fourth problem that the accuracy degrades due to the error.

In contrast, in the present embodiment, by providing the PLL circuits 120, 130, it becomes possible to forcibly match the transition timings of the clock signals CK1, CK2 with each other at every phase synchronization timing. Therefore, since it is possible to start the time-to-digital conversion process immediately after the phase synchronization timing, the first problem described above of the related art can be resolved. Further, according to the present embodiment, even in the case in which the relationship in clock frequency between the clock signals CK1, CK2 is the frequency relationship in which the transition timings do not coincide with each other, the transition timings of the clock signals CK1, CK2 are forcibly made to coincide with each other at every phase synchronization timing due to the PLL circuits 120, 130. Therefore, the second problem of the related art method can be resolved. Further, since the phase synchronization timing can be decided in a systematic manner due to the phase synchronization by the PLL circuits 120, 130, the circuit process and the circuit device can be simplified, and thus, the third problem of the related art method can be resolved. Further, since the transition timings of the clock signals CK1, CK2 coincide with each other at every phase synchronization timing, the conversion error caused by the difference in transition timing between the clock signals CK1, CK2 can be reduced, and thus, the fourth problem of the related art method can also be resolved.

Further, in the present embodiment, the phase synchronization of the clock signals CK1, CK2 is performed using a plurality of PLL circuits, namely the PLL circuits 120, 130. By using the plurality of PLL circuits 120, 130 as described above, the frequency of the phase comparison (phase synchronization) can be increased compared to the case of using a single PLL circuit, and thus, it is possible to set the frequency of the correction of the clock frequency of the clock signal using the phase comparison high frequency. For example, in the method of using a single PLL circuit alone, the length of the period in which the phase comparison is performed becomes long. According to the method of using the plurality of PLL circuits 120, 130, the period in which the phase comparison is performed can be shortened. Therefore, the correction of the clock frequency due to the phase comparison becomes to be more frequently performed, and thus, the phase error, the jitter, and so on of the clock signals CK1, CK2 can be reduced. Therefore, it is possible to minimize, for example, the error caused by the time difference in transition timing between the clock signals CK1, CK2 at the phase synchronization timing, and it becomes possible to achieve the improvement in accuracy of the time-to-digital measurement.

The oscillation circuits 101, 102 are circuits for oscillating the resonators XTAL1, XTAL2. For example, the oscillation circuit 101 (the first oscillation circuit) oscillates the resonator XTAL1 (the first resonator) to generate the clock signal CK1 with the clock frequency f1. The oscillation circuit 102 (the second oscillation circuit) oscillates the resonator XTAL2 (the second resonator) to generate the clock signal CK2 with the clock frequency f2. For example, the clock frequencies have a relationship of f1>f2.

The resonators (XTAL1, XTAL2, and XTAL3) are each, for example, a piezoelectric resonator. Specifically, the resonators are each, for example, a quartz crystal resonator. As the quartz crystal resonator, there can be cited a quartz crystal resonator vibrating in a thickness-shear mode having the cutting angle of, for example, AT-cut or SC-cut. For example, the resonator can also be a resonator incorporated in an oven-controlled crystal oscillator (OCXO) provided with a thermostatic oven, a resonator incorporated in a temperature compensated crystal oscillator (TCXO) not provided with a thermostatic oven, a resonator incorporated in a simple package crystal oscillator (SPXO), or the like. Further, as the resonators, it is also possible to adopt a surface acoustic wave (SAW) resonator, an MEMS (micro electro-mechanical systems) resonator as a silicon resonator formed using a silicon substrate, and so on.

As described above, in FIG. 1, the clock signal CK1 is a clock signal generated using the resonator XTAL1, and the clock signal CK2 is a clock signal generated using the resonator XTAL2. Further, the reference clock signal CKR can also be generated using the resonator XTAL3. By using the clock signals generated by the resonators as described above, it is possible to achieve an improvement in accuracy of the time-to-digital conversion and so on compared to the method not using the resonator. It should be noted that the present embodiment is not limited to this configuration, but it is sufficient for the clock signals CK1, CK2, and the reference clock signal CKR to be different in clock frequency from each other, and it is also possible to use clock signals from oscillators each having an oscillation circuit and a resonator housed in a package.

Figure 2:
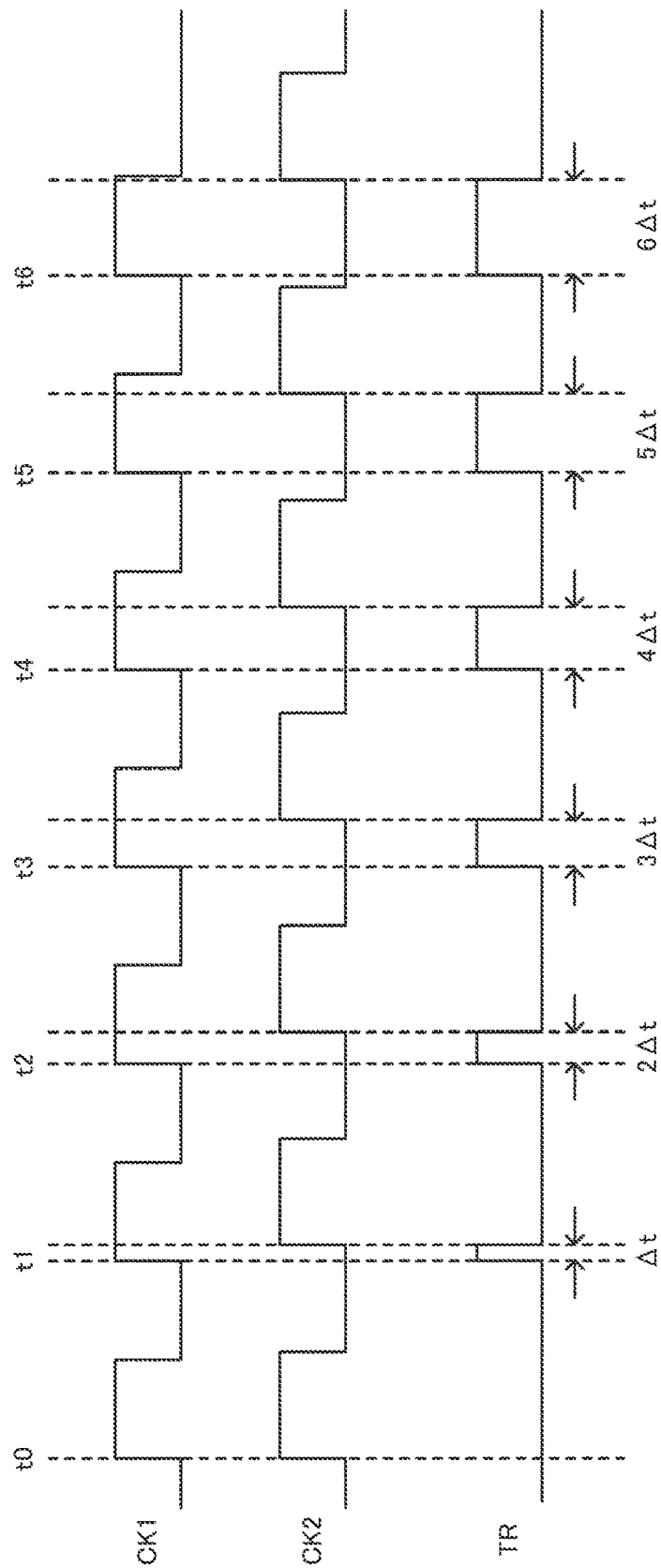
FIG. 2 is an explanatory diagram of a time-to-digital conversion method using a clock frequency difference.

FIG. 2 is an explanatory diagram of the time-to-digital conversion method using a clock frequency difference. At t0, the clock signals CK1, CK2 coincide in transition timing (phase) with each other. Subsequently, at t1, t2, t3, . . . , an inter-clock time difference TR (phase difference), which is a time difference in the transition timing between the clock signals CK1, CK2, increases monotonically like Δt, 2×Δt, 3×Δt, . . . . In FIG. 2, the inter-clock time difference is represented by a pulse signal with a width of TR.

Further, in the time-to-digital conversion of the present embodiment, there is used, for example, a plurality of resonators to convert the time into a digital value DQ using the clock frequency difference. Specifically, in the case of defining the clock frequencies of the clock signals CK1, CK2 respectively as f1, f2, the time-to-digital conversion circuit converts the time into the digital value DQ with the resolution corresponding to the frequency difference |f1−f2| between the clock frequencies f1, f2. For example, as shown in FIG. 2, the time-to-digital conversion circuit 20 converts the time into the digital value DQ using the principles of a vernier caliper.

By adopting this process, it becomes possible to set the resolution of the time-to-digital conversion using the frequency difference |f1−f2| between the clock frequencies f1, f2, and the improvement in performance such as accuracy and resolution of the time-to-digital conversion becomes possible.

Specifically, the resolution (time resolution) Δt of the time-to-digital conversion of the present embodiment can be expressed as follows.

$$\Delta t = |1/f1 - 1/f2| = |f1 - f2|/(f1 \times f2)$$

Further, the time-to-digital conversion circuit 20 converts the time into the digital value DQ with the resolution Δt expressed as follows.

$$\Delta t = |1/f1 - 1/f2| = |f1 - f2|/(f1 \times f2)$$

The resolution Δt is expressed as follows, and corresponds to the frequency difference |f1−f2|.

$$\Delta t = |f1 - f2|/(f1 \times f2)$$

By adopting this process, it becomes possible to set the resolution of the time-to-digital conversion by setting the clock frequencies f1, f2. For example, by decreasing the frequency difference |f1−f2| between the clock frequencies f1, f2, the resolution Δt can be made finer, and it becomes possible to realize the time-to-digital conversion high in resolution. Further, by setting the clock frequencies f1, f2 to high frequencies, the resolution Δt can be made finer, and it becomes possible to realize the time-to-digital conversion high in resolution. Further, by generating the clock signals CK1, CK2 having the clock frequencies f1, f2 using the resonators XTAL1, XTAL2 or the like, it becomes possible to achieve an improvement in accuracy of the time-to-digital conversion compared to the case of using a delay element formed of a semiconductor element.

Figure 3:
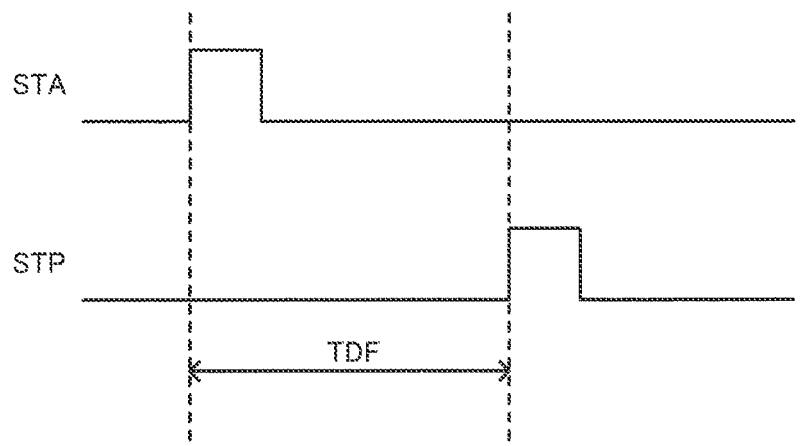
FIG. 3 is a diagram showing a relationship between signals STA, STP.

FIG. 3 is a diagram showing a relationship between the signal STA (the first signal, the start signal) and the signal STP (the second signal, the stop signal). The time-to-digital conversion circuit 20 of the present embodiment converts the time difference TDF in transition timing between the signal STA and the signal STP into a digital value. It should be noted that although in FIG. 3, TDF is defined as the time difference between (between the rising edges) the transition timings of the rising edges of the signal STA and the signal STP, but can also be defined as the time difference between (between the falling edges) the transition timings of the falling edges of the signal STA and the signal STP.

Figure 4:
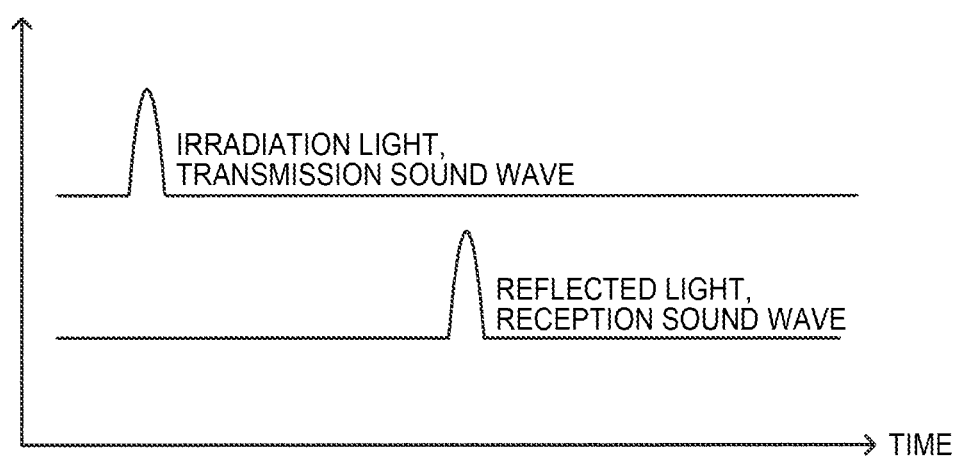
FIG. 4 is a diagram showing an example of physical quantity measurement using the signals STA, STP.

FIG. 4 is a diagram showing an example of physical quantity measurement using the signals STA, STP. For example, the physical quantity measurement device including the circuit device 10 according to the present embodiment emits the irradiation light (e.g., a laser beam) to an object (e.g., an object in the periphery of a car) using the signal STA. Then, the signal STP is generated due to the reception of the reflected light from the object. For example, the physical quantity measurement device performs waveform shaping on the light reception signal to thereby generate the signal STP. According to this process, by converting the time difference TDF in transition timing between the signal STA and the signal STP into a digital value, the distance from the object can be measured as a physical quantity using, for example, a time-of-flight (TOF) method, and can be used for, for example, automated driving of a car.

Alternatively, the physical quantity measurement device transmits a transmission sound wave (e.g., an ultrasonic wave) to an object (e.g., a living body) using the signal STA. Then, the signal STP is generated due to the reception of the reception sound wave from the object. For example, the physical quantity measurement device performs waveform shaping on the reception sound wave to thereby generate the signal STP. According to this process, by converting the time difference TDF in the transition timing between the signal STA and the signal STP into a digital value, the distance from the object and so on can be measured, and the measurement of biological information and so on using an ultrasonic wave becomes possible.

It should be noted that in FIG. 3 and FIG. 4, it is also possible to measure the time from when the transmission data is transmitted to when the reception data is received by transmitting the transmission data with the signal STA, and using the signal STP due to the reception of the reception data. Further, the physical quantity measured by the physical quantity measurement device according to the present embodiment is not limited to the time and the distance, but a variety of physical quantities such as a flow rate, flow speed, a frequency, speed, acceleration, angular velocity, and angular acceleration are conceivable.

2. First Configuration Example

Figure 5:
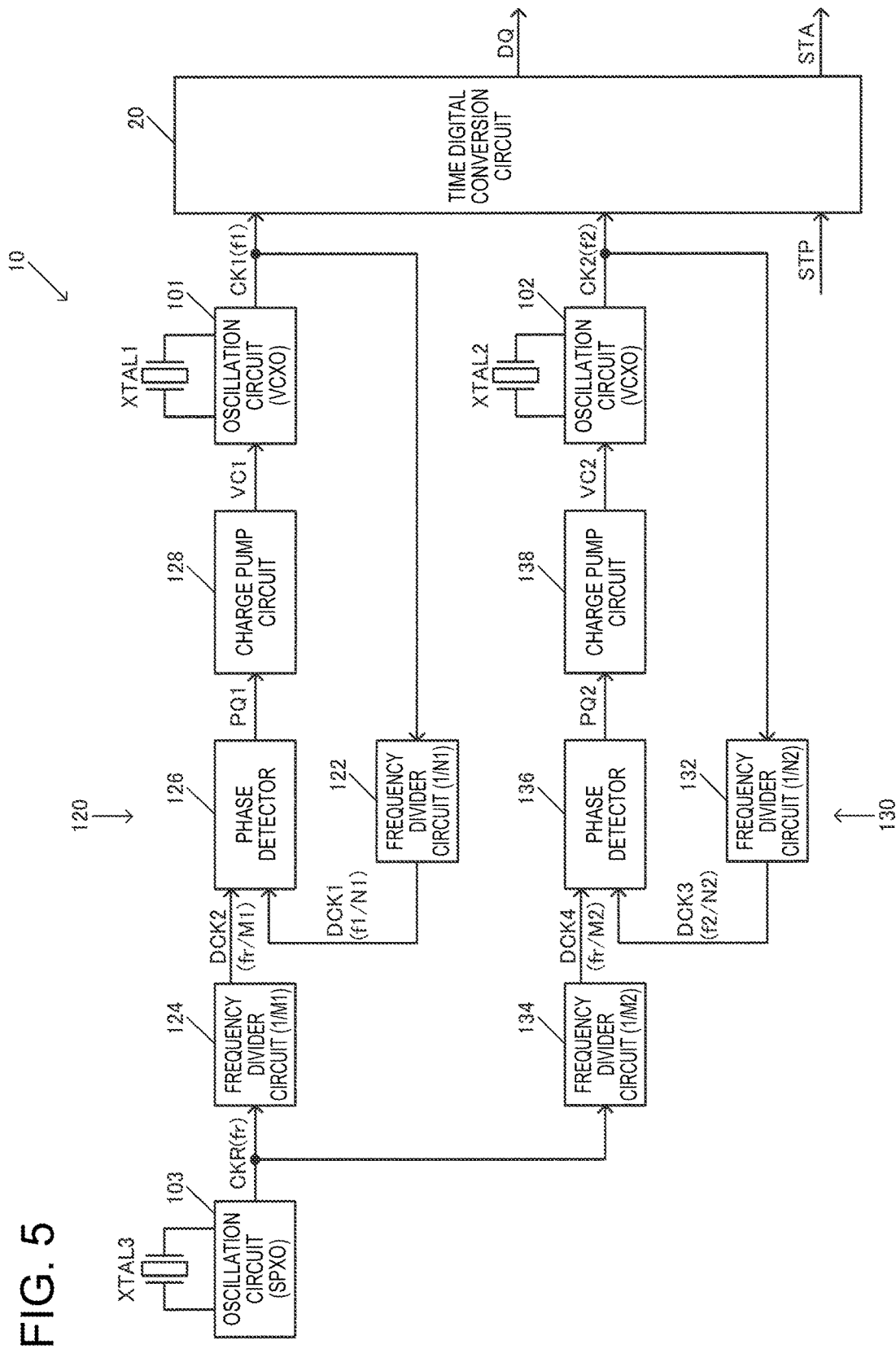
FIG. 5 is a diagram showing a detailed first configuration example of the circuit device according to the embodiment.

FIG. 5 shows a detailed first configuration example of the circuit device 10 according to the present embodiment. FIG. 5 shows a specific configuration example of the PLL circuits 120, 130.

The PLL circuit 120 shown in FIG. 5 includes frequency divider circuits 122, 124 (first and second frequency divider circuits) and a phase detector 126 (a first phase comparator). The frequency divider circuit 122 divides the frequency of the clock signal CK1 to output a frequency-divided clock signal DCK1 (a first frequency-divided clock signal). Specifically, the frequency divider circuit 122 performs frequency division of reducing the clock frequency f1 of the clock signal CK1 to 1/N1 to output the frequency-divided clock signal DCK1 having a clock frequency of f1/N1.

The frequency divider circuit 124 divides the frequency of the reference clock signal CKR to output a frequency-divided clock signal DCK2 (a second frequency-divided clock signal). Specifically, the frequency divider circuit 124 performs the frequency division of reducing the clock frequency fr of the clock signal CKR to 1/M1 to output the frequency-divided clock signal DCK2 having a clock frequency of fr/M1. Then, the phase detector 126 performs phase comparison between the frequency-divided clock signal DCK1 and the frequency-divided clock signal DCK2.

Specifically, the frequency divider circuit 122 has a counter for the frequency division for performing the counting operation of the count value based on the clock signal CK1, and the counter is reset when the count value reaches, for example, N1. The frequency divider circuit 124 has a counter for the frequency division for performing the counting operation of the count value based on the clock signal CKR, and the counter is reset when the count value reaches, for example, M1.

Further, the circuit device 10 includes the oscillation circuit 101. The oscillation circuit 101 is controlled based on the phase comparison result of the phase detector 126 of the PLL circuit 120, and oscillates the resonator XTAL1. The oscillation circuit 101 is also a constituent of, for example, the PLL circuit 120. Specifically, the oscillation circuit 101 is, for example, a voltage-controlled oscillation circuit (VCXO) the oscillation frequency of which is controlled using voltage control.

Figure 12:
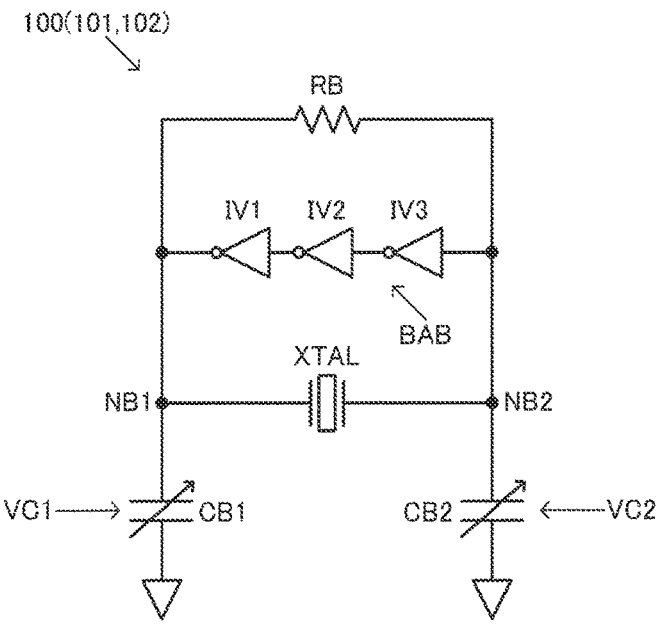
FIG. 12 is a diagram showing a first configuration example of an oscillation circuit.
Figure 13:
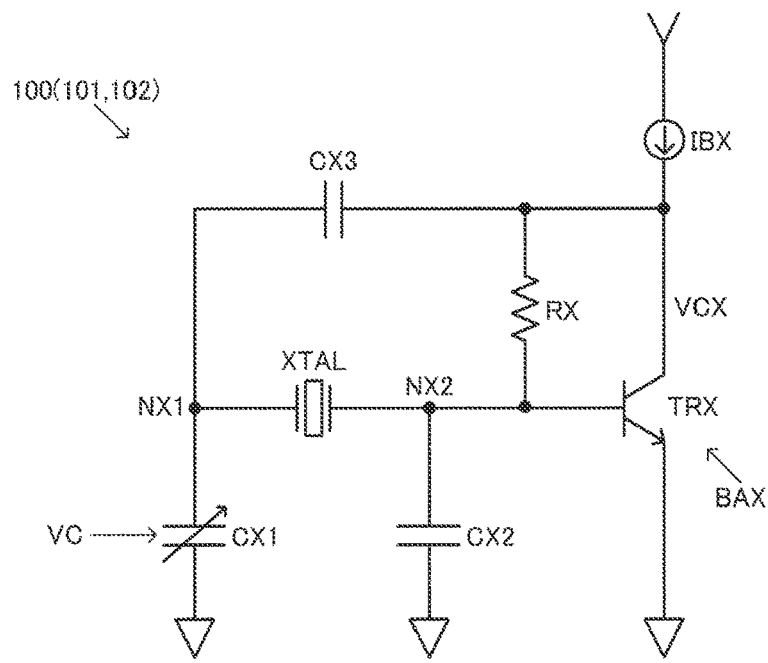
FIG. 13 is a diagram showing a second configuration example of the oscillation circuit.

Then, the PLL circuit 120 includes a charge pump circuit 128, and the phase detector 126 outputs a signal PQ1 as the phase comparison result to the charge pump circuit 128. The signal PQ1 is, for example, an up/down signal, and the charge pump 128 outputs a control voltage VC1, which is based on the signal PQ1, to the oscillation circuit 101. The charge pump circuit 128 includes a loop filter (alternatively, the loop filter is disposed in a posterior stage of the charge pump circuit 128), and the loop filter converts the up/down signal as the signal PQ1 into the control voltage VC1. The oscillation circuit 101 performs the oscillation operation of the resonator XTAL1, the oscillation frequency of which is controlled based on the control voltage VC1, to generate the clock signal CK1. For example, as shown in FIG. 12 and FIG. 13, the oscillation circuit 101 has a variable capacitance circuits (CB1, CB2, CX1), and the capacitance values of the variable capacitance circuits are controlled based on the control voltage VC (VC1, VC2) to thereby control the oscillation frequency.

Specifically, the phase detector 126 outputs an up signal as the signal PQ1 in the case in which the phase of the frequency-divided clock signal DCK1 as a feedback signal lags in phase behind the frequency-divided clock signal DCK2 as a reference signal. In contrast, in the case in which the frequency-divided clock signal DCK1 leads in phase over the frequency-divided clock signal DCK2, the phase detector 126 outputs a down signal as the signal PQ1.

The charge pump circuit 128 for performing the charge pump operation includes an up-transistor and a down-transistor connected in series between, for example, VDD (a high potential side power supply voltage) and VSS (a low potential side power supply voltage). Then, when the up signal is activated, the up-transistor is set to an ON state. Thus, a charge operation of the capacitor provided to the loop filter is performed, and the control voltage VC1 changes toward VDD. When the control voltage VC1 changes toward VDD, the oscillation frequency of the oscillation circuit 101 changes toward the high frequency side, and the clock frequency f1 of the clock signal CK1 also changes toward the high frequency side. On the other hand, when the down signal is activated, the down-transistor is set to the ON state. Thus, a discharge operation of the capacitor provided to the loop filter is performed, and the control voltage VC1 changes toward VSS. When the control voltage VC1 changes toward VSS, the oscillation frequency of the oscillation circuit 101 changes toward the low frequency side, and the clock frequency f1 of the clock signal CK1 also changes toward the low frequency side.

The PLL circuit 130 includes frequency divider circuits 132, 134 (third and fourth frequency divider circuits) and a phase detector 136 (a second phase comparator). The frequency divider circuit 132 divides the frequency of the clock signal CK2 to output a frequency-divided clock signal DCK3 (a third frequency-divided clock signal). Specifically, the frequency divider circuit 132 performs the frequency division of reducing the clock frequency f2 of the clock signal CK2 to 1/N2 to output the frequency-divided clock signal DCK3 having a clock frequency of f2/N2.

The frequency divider circuit 134 divides the frequency of the reference clock signal CKR to output a frequency-divided clock signal DCK4 (a fourth frequency-divided clock signal). Specifically, the frequency divider circuit 134 performs the frequency division of reducing the clock frequency fr of the clock signal CKR to 1/M2 to output the frequency-divided clock signal DCK4 having a clock frequency of fr/M2. Then, the phase detector 136 performs phase comparison between the frequency-divided clock signal DCK3 and the frequency-divided clock signal DCK4. It should be noted that since the configuration and the operation of the frequency divider circuits 132, 134 are substantially the same as those of the frequency divider circuits 122, 124, the detailed description thereof will be omitted.

Further, the circuit device 10 includes the oscillation circuit 102. The oscillation circuit 102 is controlled based on the phase comparison result of the phase detector 136 of the PLL circuit 130, and oscillates the resonator XTAL2. The oscillation circuit 102 is also a constituent of, for example, the PLL circuit 130. Specifically, the oscillation circuit 102 is, for example, a voltage-controlled oscillation circuit (VCXO), the oscillation frequency of which is controlled using voltage control.

Then, the PLL circuit 130 includes a charge pump circuit 138, and the phase detector 136 outputs a signal PQ2, which is the phase comparison result, to the charge pump circuit 138. The charge pump circuit 138 outputs a control voltage VC2 based on the signal PQ2 to the oscillation circuit 102. The charge pump circuit 138 includes a loop filter, and the up/down signal as the signal PQ2 is converted by the loop filter into the control device VC2. The oscillation circuit 102 performs the oscillation operation of the resonator XTAL2, the oscillation frequency of which is controlled based on the control voltage VC2, to generate the clock signal CK2. It should be noted that since the configuration and the operation of the phase detector 136, the charge pump circuit 138 and the oscillation circuit 102 are substantially the same as those of the phase detector 126, the charge pump circuit 128 and the oscillation circuit 101, and the detailed description thereof will be omitted.

Further, the circuit device 10 includes the oscillation circuit 103 (the third oscillation circuit), and the oscillation circuit 103 oscillates the resonator XTAL3 to generate the reference clock signal CKR. As the resonator XTAL3, a quartz crystal resonator, for example, can be used. By using the quartz crystal resonator, it is possible to generate the reference clock signal CKR small in jitter and phase error, and high in accuracy, and as a result, the jitter and the phase error of the clock signals CK1, CK2 can also be reduced, and it becomes possible to achieve high-accuracy time-to-digital conversion.

Figure 6:
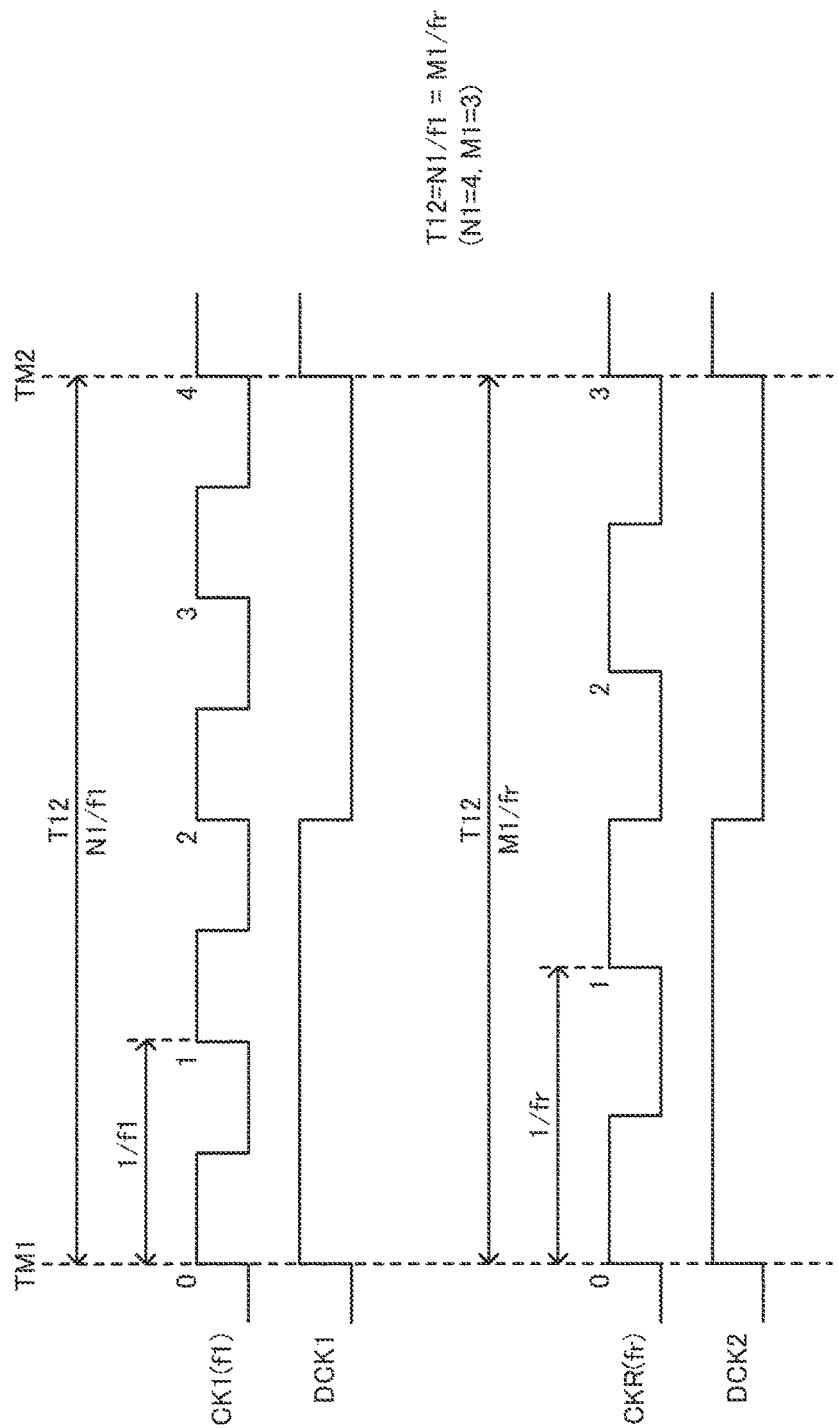
FIG. 6 is a signal waveform chart for explaining an operation of the circuit device.
Figure 7:
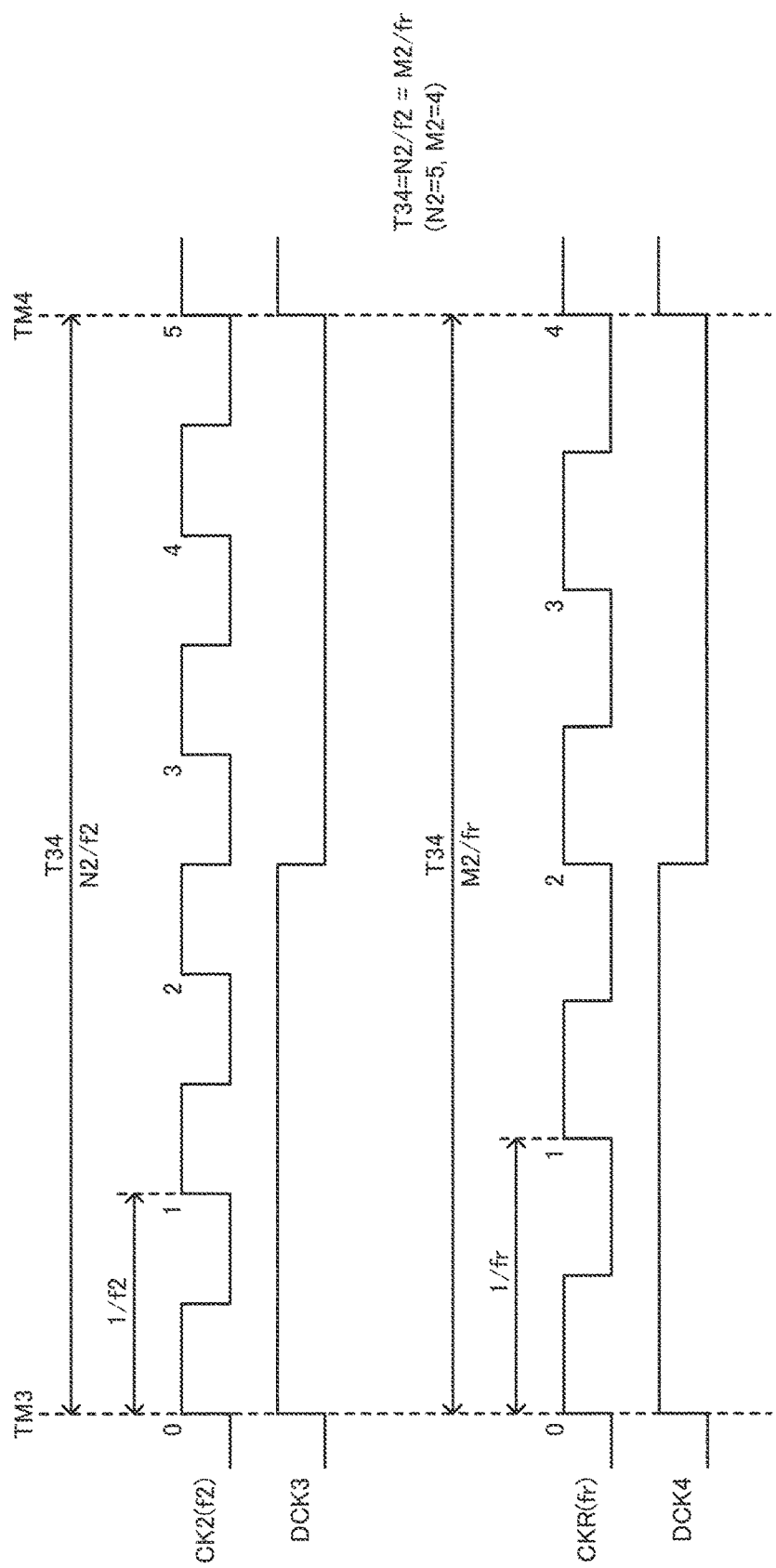
FIG. 7 is a signal waveform chart for explaining an operation of the circuit device.

FIG. 6 and FIG. 7 are signal waveform charts for explaining the operation of the circuit device 10 according to the present embodiment. It should be noted that although in FIG. 6 and FIG. 7, there is shown an example in which N1=4, M1=3, N2=5, and M2=4 are set for the sake of simplification of the description, in reality, in order to increase the resolution of the time-to-digital conversion, N1, M1, N2 and M2 are set to extremely large values.

FIG. 6 shows the case in which the phase synchronization between the clock signal CK1 and the reference clock signal CKR is achieved by the PLL circuit 120, and the PLL circuit 120 is in a locked state.

As shown in FIG. 6, the signal obtained by frequency-dividing the clock signal CK1 by N1=4 becomes the frequency-divided clock signal DCK1. Further, the signal obtained by frequency-dividing the clock signal CKR by M1=3 becomes the frequency-divided clock signal DCK2. As described above, the phase detector 126 performs the phase comparison between the frequency-divided clock signals DCK1, DCK2, and there is performed the feedback control for controlling the oscillation frequency of the oscillation circuit 101 based on the phase comparison result. Thus, the transition timings (the rising edges) of the frequency-divided clock signals DCK1, DCK2 become to coincide (roughly coincide) with each other at the phase synchronization timings TM1, TM2, and the transition timings of the clock signal CK1 and the reference clock signal CKR also become to coincide (roughly coincide) with each other.

For example, in FIG. 6, the period between the phase synchronization timings TM1, TM2 is defined as T12. The length of the time of one clock cycle of the clock signal CK1 with the clock frequency f1 is 1/f1. Further, the length of the time of one clock cycle of the reference clock signal CKR with the clock frequency fr is 1/fr. Further, the PLL circuit 120 performs the feedback control so that the transition timings of the frequency-divided clock signals DCK1, DCK2 coincide with each other at the phase synchronization timings TM1, TM2. Thus, the length of the period T12 becomes N1/f1, which is the length corresponding to N1 clock cycles of the clock signal CK1. Further, the length of the period T12 becomes M1/fr, which is the length corresponding to M1 clock cycles of the reference clock signal CKR. In other words, the PLL circuit 120 performs the phase synchronization between the clock signal CK1 and the reference clock signal CKR so that the relationship of T12=N1/f1=M1/fr becomes true.

FIG. 7 shows the case in which the phase synchronization between the clock signal CK2 and the reference clock signal CKR is achieved by the PLL circuit 130, and the PLL circuit 130 is in a locked state.

As shown in FIG. 7, the signal obtained by frequency-dividing the clock signal CK2 by N2=5 becomes the frequency-divided clock signal DCK3. Further, the signal obtained by frequency-dividing the clock signal CKR by M2=4 becomes the frequency-divided clock signal DCK4. As described above, the phase detector 136 performs the phase comparison between the frequency-divided clock signals DCK3, DCK4, and there is performed the feedback control for controlling the oscillation frequency of the oscillation circuit 102 based on the phase comparison result. Thus, the transition timings (the rising edges) of the frequency-divided clock signals DCK3, DCK4 become to coincide (roughly coincide) with each other at the phase synchronization timings TM3, TM4, and the transition timings of the clock signal CK2 and the reference clock signal CKR also become to coincide (roughly coincide) with each other.

For example, in FIG. 7, the period between the phase synchronization timings TM3, TM4 is defined as T34. The length of the time of one clock cycle of the clock signal CK2 with the clock frequency f2 is 1/f2. Further, the length of the time of one clock cycle of the reference clock signal CKR is 1/fr. Further, the PLL circuit 130 performs the feedback control so that the transition timings of the frequency-divided clock signals DCK3, DCK4 coincide with each other at the phase synchronization timings TM3, TM4. Thus, the length of the period T34 becomes N2/f2, which is the length corresponding to N2 clock cycles of the clock signal CK2. Further, the length of the period T34 becomes M2/fr, which is the length corresponding to M2 clock cycles of the reference clock signal CKR. In other words, the PLL circuit 130 performs the phase synchronization between the clock signal CK2 and the reference clock signal CKR so that the relationship of T34=N2/f2=M2/fr becomes true.

Figure 8:
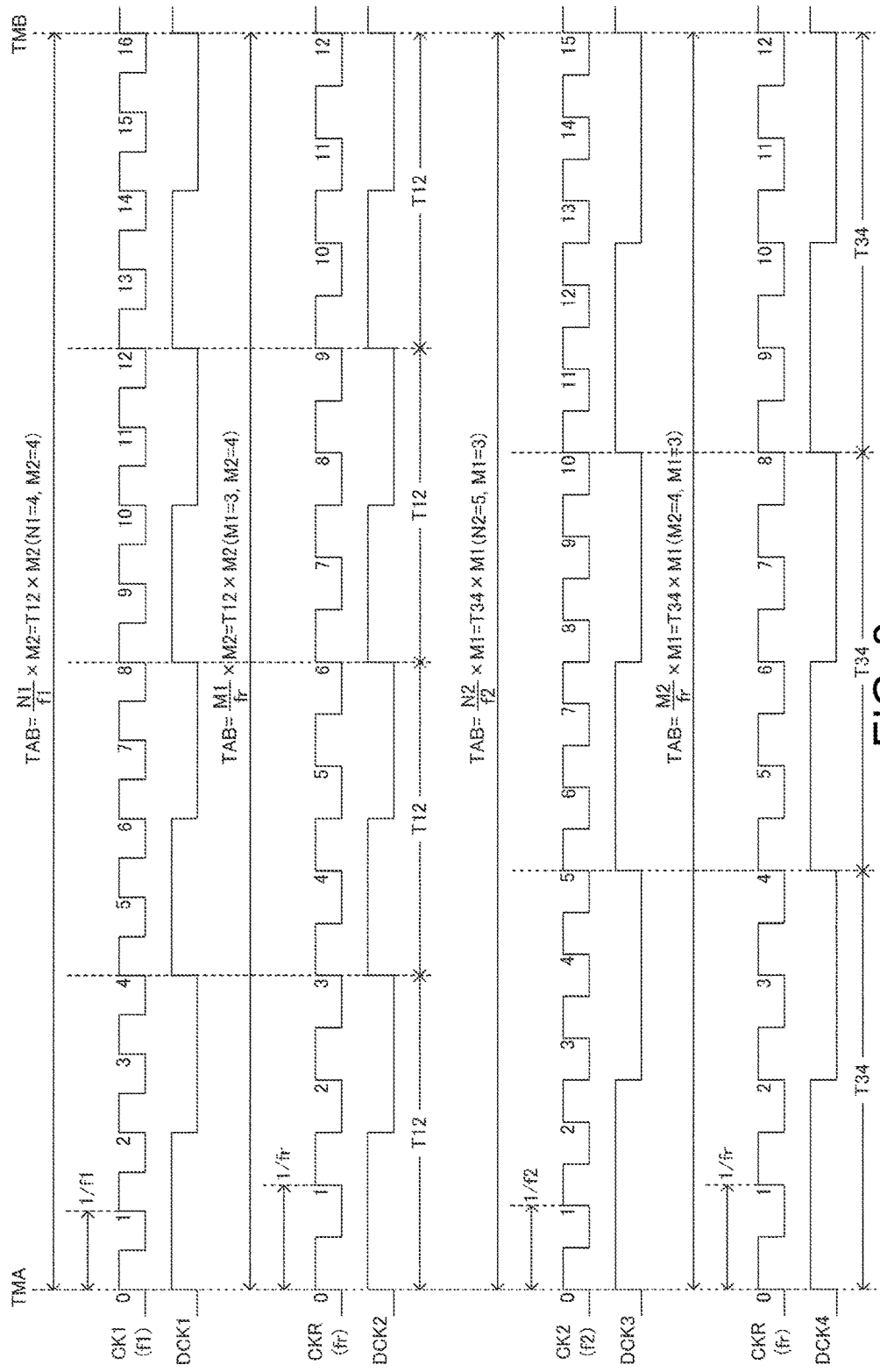
FIG. 8 is a signal waveform chart for explaining an overall operation of the circuit device.

FIG. 8 is a signal waveform chart for explaining the overall operation of the circuit device 10 according to the present embodiment. As described with reference to FIG. 6, the phase synchronization between the clock signal CK1 and the reference clock signal CKR is achieved by the PLL circuit 120 at intervals of the period T12. As described with reference to FIG. 7, the phase synchronization between the clock signal CK2 and the reference clock signal CKR is achieved by the PLL circuit 130 at intervals of the period T34. Thus, it results that the clock signals CK1, CK2 are phase-synchronized with each other at intervals of the period TAB.

The period TAB is a period between the phase synchronization timings TMA, TMB of the clock signals CK1, CK2, and as shown in FIG. 8, the relationship of TAB=T12×M2=T34×M1 is true. For example, in the case in which M2=4, M1=3 are true, TAB=T12×4=T34×3 becomes true. Here, as described above with reference to FIG. 6 and FIG. 7, the relationships of T12=N1/F1=M1/fr, T34=N2/F2=M2/fr are true.

The frequency division ratios N1, M1, N2, and M2 of the respective frequency divider circuits 122, 124, 132, and 134 shown in FIG. 5 are actually set to extremely large numbers. FIG. 9 shows an example of setting of the frequency division ratios. For example, in the case in which the clock frequency fr of the reference clock signal CKR is fr=101 MHz, by setting the frequency division ratios N1, M1 of the frequency divider circuits 122, 124 shown in FIG. 5 to N1=101, M1=100, the clock signal CK1 with the frequency f1=102.01 MHz is generated by the PLL circuit 120. Further, by setting the frequency division ratios N2, M2 of the frequency divider circuits 132, 134 to N2=102, M2=101, the clock signal CK2 with the frequency f2=102 MHz is generated by the PLL circuit 130. Thus, it is possible to set the resolution (time resolution) Δt of the time-to-digital conversion described with reference to FIG. 2 to Δt=|1/f1−1/f2|=0.96 ps (picosecond), and it becomes possible to realize the time-to-digital conversion extremely high in resolution.

As shown in FIGS. 9, N1 and M1 are integers no smaller than 2 and different from each other, and N2 and M2 are also integers no smaller than 2 and different from each other. Further, at least one of N1 and M1, and at least one of N2 and M2 are integers different from each other. Further, preferably, N1 and N2 have the greatest common divisor of 1, and the least common multiple of N1×N2, and M1 and M2 have the greatest common divisor of 1, and the least common multiple of M1×M2.

Further, in FIG. 9, the relationship of |N1×M2−N2×M1|=1 is true. In other words, N1, M1, N2, and M2 are set so that the relationship of |N1×M2−N2×M1|=1 becomes true. Taking the case of FIG. 8 in which N1=4, M1=3, N2=5, and M2=4 are set as an example, |N1×M2−N2×M1|=|4×4−5×3|=1 is obtained. This means that the length corresponding to 16 cycles of the clock signal CK1 is equal to the length corresponding to 15 cycles of the clock signal CK2. Specifically, as shown in FIG. 8, this means that the following is true.

$$TAB=(N1/f1)\times M2=(4/f1)\times 4=(1/f1)\times 16=(N2/f2)\times M1=(5/f2)\times 3=(1/f2)\times 15$$

According to this process, the clock signal CK1 and the clock signal CK2 become shifted from each other as much as one clock cycle (one clock period) in every period TAB. Thus, it becomes possible to easily realize the time-to-digital conversion using the principle of a vernier caliper (vernier) shown in FIG. 10 described later.

For example, as a method of a comparative example of the present embodiment, there can be adopted a method of achieving the phase synchronization between the clock signals CK1, CK2 using a single PLL circuit. Taking the case of FIG. 8 as an example, in the method, the phase comparison between the clock signals CK1, CK2 is performed at intervals of the period TAB to achieve the phase synchronization. However, according to the method of this comparative example, since the frequency of performing the phase comparison decreases to increase the length of the period TAB for performing the phase synchronization, there is a disadvantage that the jitter and the phase noise of the clock signals CK1, CK2 increase.

In contrast, in FIG. 8, the phase synchronization between the clock signal CK1 and the reference clock signal CKR is performed at intervals of the period T12 shorter than the period TAB, and the phase synchronization between the clock signal CK2 and the reference clock signal CKR is performed at intervals of the period T34 shorter than the period TAB. Therefore, the frequency of performing the phase comparison becomes higher compared to the method of the comparative example described above, and it becomes possible to achieve reduction of the jitter and the phase noise of the clock signals CK1, CK2, and so on. In particular in the case of setting N1, M1, N2, and M2 to large numbers in order to realize the resolution Δt as a high resolution as shown in FIG. 9, the length of the period TAB becomes extremely long in the method of the comparative example described above, and the error is accumulated to thereby increase the jitter and the phase error. Therefore, since the frequency division ratio of the frequency divider circuit in the PLL circuit is set to an extremely large number, a harmful influence of the cumulative error becomes large. In contrast, in the case of FIG. 8, since the phase comparison is performed at intervals of the periods T12, T34 shorter than the period TAB, there is an advantage that the cumulative error can be decreased, and thus, the jitter and the phase error can be improved. In other words, since the frequency division ratio of the frequency divider circuit can be set to a small number compared to the method of the comparative example, the harmful influence of the cumulative error can be reduced.

Figure 10:
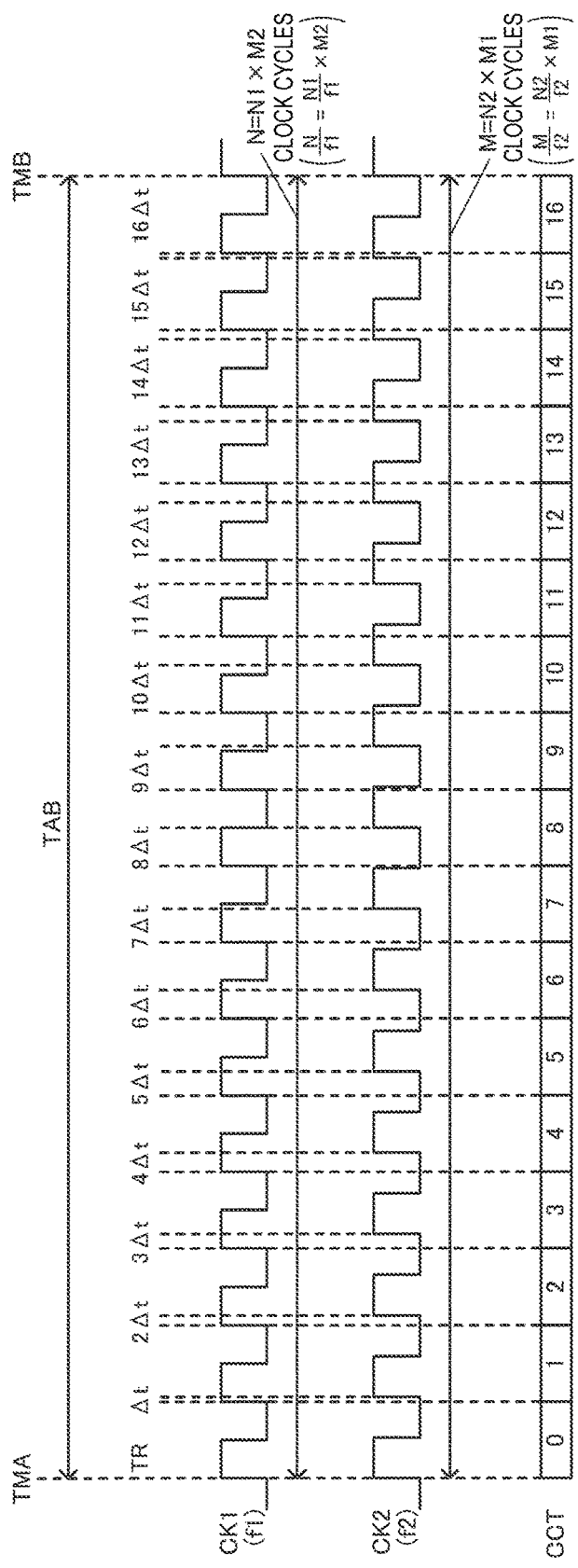
FIG. 10 is a signal waveform chart for explaining a detailed operation of the circuit device.

FIG. 10 is a signal waveform chart for explaining the detailed operation of the circuit device 10 according to the present embodiment. In FIG. 10, at the phase synchronization timing TMA, the phase synchronization by the PLL circuits 120, 130 is achieved, and thus, the transition timings of the clock signals CK1, CK2 coincide with each other. Subsequently, as described with reference to FIG. 2, the time difference in transition timing between the clock signals CK1, CK2 continues to increase by Δt in every clock cycle (CCT) in such a manner as Δt, 2×Δt, 3×Δt, . . . . Then, at the phase synchronization timing TMB, the phase synchronization by the PLL circuits 120, 130 is achieved, and thus, the transition timings of the clock signals CK1, CK2 coincide with each other.

As shown in FIG. 10, the length of the period TAB between the phase synchronization timings TMA, TMB is made to correspond to N (=N1×M2) clock cycles of the clock signal CK1. Therefore, TAB=(N1/f1)×M2 is obtained. Taking the case of FIG. 8 in which N1=4, M2=4 are set as an example, the length of the period TAB is made to correspond to 16 clock cycles of the clock signal CK1. Further, the length of the period TAB is made to correspond to M (=N2×M1) clock cycles of the clock signal CK2. Therefore, TAB=(N2/f2)×M1 is obtained. Taking the case of FIG. 8 in which N2=5, M1=3 are set as an example, the length of the period TAB is made to correspond to 15 clock cycles of the clock signal CK1. As described above, in FIG. 10, the relationship of TAB=(N1/f1)×M2=(N2/f2)×M1 is true. For example, defining N and M as N=N1×M2, M=N2×M1, the relationship of N/f1=M/f2 is true.

Further, as explained with reference to FIG. 8, the relationship of |N1×M2−N2×M1|=|4×4−5×3|=1 is true. Thus, as shown in FIG. 10, the clock signals CK1, CK2 become to be shifted from each other as much as one clock cycle in every period TAB.

By adopting this configuration, as shown in FIG. 10, the inter-clock time difference TR between the clock signals CK1, CK2 becomes to increase by Δt in such a manner as Δt, 2×Δt, 3×Δt, . . . after the transition timings of the clock signals CK1, CK2 coincide with each other at the phase synchronization timing TMA. Therefore, it is possible to create the inter-clock time difference TR between the clock signals CK1, CK2 continues to increase by Δt in every clock cycle after the phase synchronization timing TMA. Then, at the subsequent phase synchronization timing TMB, the transition timings of the clock signals CK1, CK2 coincide with each other, and thus the inter-clock time difference TR becomes zero. Subsequently, the inter-clock time difference TR becomes to increase by Δt in every clock cycle.

As described above, by creating the inter-clock time difference TR vanishing at the phase synchronization timing, and then continuing to increase by Δt (the resolution) due to the phase synchronization by the PLL circuits 120, 130, it becomes possible to realize the process of the time-to-digital conversion (a repeating method, an updating method, and a binary method) described later. Specifically, it is possible to realize the time-to-digital conversion for converting the time into the digital value with the resolution Δt using the principle of a vernier caliper (vernier). Further, in such a process of the time-to-digital conversion with the resolution Δt, since the inter-clock time difference TR in each clock cycle (CCT) in the period TAB can uniquely be identified as shown in FIG. 10, it is possible to achieve simplification of the process and the circuit configuration of the time-to-digital conversion. Further, due to the phase synchronization by the PLL circuits 120, 130, since it is possible to make the transition timings of the clock signals CK1, CK2 coincide (roughly coincide) with each other at the phase synchronization timings TMA, TMB, it becomes possible to achieve an improvement in the accuracy of the time-to-digital conversion, and so on.

For example, as the method of a comparative example of the present embodiment, it is possible to adopt a method of setting a design clock frequency so that the relationship of N/f1=M/f2 is true without performing the phase synchronization using the PLL circuits 120, 130. For example, it is possible to adopt a method of making the relationship of N/f1=M/f2 true as the relationship of the design clock frequencies of the first and second quartz crystal oscillators in the related art method of Document 4 described above. It should be noted that in FIG. 10, TAB=(N1/f1)×M2=(N2/f2)×M1 is true, and defining N, M as N=N1×M2, M=N2×M1, the relationship of N/f1=M/f2 is true.

However, in the related art method described above, the first and second quartz crystal oscillators each perform a free-running oscillation operation in which the oscillation operation is not controlled. Therefore, even if the relationship of N/f1=M/f2 is true, it is difficult to make the transition timings of the clock signals CK1, CK2 coincide with each other at the phase synchronization timings. For example, since the first and second quartz crystal oscillators are different in start-up timing of the oscillation from each other, in the method according to the comparative example in which such phase synchronization as in the present embodiment is not performed, it is not possible to make the transition timings of the clock signals CK1, CK2 coincide with each other at the phase synchronization timings. Further, the clock frequencies by the first and second quartz crystal oscillators vary due to a manufacturing variation or an environmental variation such as a temperature variation. Therefore, even if the relationship of N/f1=M/f2 is made true at the design phase, the relationship of N/f1=M/f2 becomes no longer true in the actual product. Therefore, a shift or the like occurs in the transition timing, and therefore, the conversion accuracy of the time-to-digital conversion degrades.

In contrast, in the present embodiment, even in the case in which the variation of the clock frequency due to the manufacturing variation or the environmental variation occurs, the PLL circuits 120, 130 adjust the oscillation frequencies of the oscillation circuits 101, 102 based on the control voltages VC1, VC2, and thus, the clock frequencies f1, f2 are adjusted so that the variations are compensated. Therefore, even in the case in which such variations of the clock frequencies occur, it becomes possible to make the relationship of N/f1=M/f2 true, and thus, it becomes possible to realize the appropriate time-to-digital conversion. Further, as shown in FIG. 7, since it is possible to make the transition timings of the clock signals CK1, CK2 coincide with each other at the phase synchronization timings TMA, TMB, it becomes possible to prevent the degradation of the conversion accuracy due to the shift of the transition timing to thereby achieve an improvement in the performance of the time-to-digital conversion.

As described above, in the present embodiment, in the case of defining the clock frequencies of the clock signals CK1, CK2 as f1, f2, the PLL circuits 120, 130 perform the phase synchronization between the clock signals CK1, CK2 so as to fulfill N/f1=M/f2. Specifically, the phase synchronization is performed so as to fulfill (N1/f1)×M2=(N2/f2)×M1.

By adopting this configuration, the phase synchronization at an appropriate phase synchronization timing becomes possible, and it is possible to prevent occurrence of a trouble caused by the phase synchronization at inappropriate phase synchronization timing, and so on. Specifically, in the repeating method of the signal STA explained with reference to FIG. 16 and FIG. 17 described later, the time-to-digital conversion using the period TAB as the measurement period (TS) becomes possible. Further, in the updating method of the clock cycle designation value and the binary search method explained with reference to FIG. 18 through FIG. 21 described later, the time-to-digital conversion using the period TAB as the updating period (TP, TP1 through TP4) becomes possible. Therefore, the time-to-digital conversion using the period TAB as the processing period becomes possible, and it becomes possible to achieve simplification of the processing sequence and the circuit configuration and so on.

Further, in the case of defining the resolution of the time-to-digital conversion as $\Delta t$, and N, M as N=N1×M2, M=N2×M1, the PLL circuits 120, 130 perform the phase synchronization between the clock signals CK1, CK2 so as to fulfill the following expression.

$$\Delta t=|N-M|/(N\times f2)=|N-M|/(M\times f1)$$

In other words, as shown in FIG. 8 and FIG. 10, the PLL circuits 120, 130 perform the phase synchronization so as to fulfill (N1/f1)×M2=(N2/f2)×M1, and defining N, M as N=N1×M2, M=N2×M1, the phase synchronization is performed so as to fulfill N/f1=M/f2. Further, as described with reference to FIG. 2 and FIG. 10, the resolution $\Delta t$ of the time-to-digital conversion of the present embodiment can be expressed as the following relational expression.

$$\Delta t=|f1-f2|/(f1\times f2)$$

Therefore, based on these two relational expressions, Formula (1) below becomes true.

$$\Delta t=|N-M|/(N\times f2)=|N-M|/(M\times f1) \quad (1)$$

By adopting this configuration, it becomes possible to set N=N1×M2, M=N2×M1 in accordance with the resolution $\Delta t$ required for the time-to-digital conversion to achieve the phase synchronization between the clock signals CK1, CK2.

For example, there is assumed the case in which the clock frequency fr of the reference clock signal CKR is fr=101 MHz in FIG. 9. In this case, N and M are set as N=N1×M2=101×101=10201 and M=N2×M1=102×100=10200, respectively. Here, the relationship of |N1×M2−N2×M1|=|10201−10200|=1 is true. By adopting this configuration, the clock frequencies of the clock signals CK1, CK2 are set to f1=102.01 MHz, f2=102 MHz, respectively, as shown in FIG. 9. In other words, the oscillation circuit 101 shown in FIG. 5 adjusts the clock frequency f1 of the clock signal CK1 based on the control voltage VC1 so as to achieve f1=102.01 MHz. The oscillation circuit 102 adjusts the clock frequency f2 of the clock signal CK2 based on the control voltage VC2 so as to achieve f2=102 MHz. Thus, it is possible to set the resolution $\Delta t$ of the time-to-digital conversion to 0.96 ps (picosecond) from the relational expression of $\Delta t=|N-M|/(N\times f2)=|10201-10200|/(10201\times f2)$, and it becomes possible to realize the time-to-digital conversion extremely high in resolution.

As described above, in the present embodiment, by appropriately setting N=N1×M2, M=N2×M1 fulfilling the formula (1) described above in accordance with the required resolution $\Delta t$, it becomes possible to realize the time-to-digital conversion with the resolution $\Delta t$ satisfying the requirement.

It should be noted that the magnitude relation between the clock frequencies f1, f2 is not limited to f1>f2, but can also be f1<f2. Further, in FIG. 5, it is arranged that the relationship of N/f1=M/f2 is satisfied due to the frequency division operation by the frequency divider circuits 122, 124, 132, and 134, but the present embodiment is not limited to this configuration. For example, it is also possible to realize the above with the circuit operation for achieving the frequency ratio f1/f2 satisfying f1/f2=N/M. For example, the relationship of f1/f2=N/M can be realized by the PLL circuits 120, 130 of a fractional division type.

Figure 11:
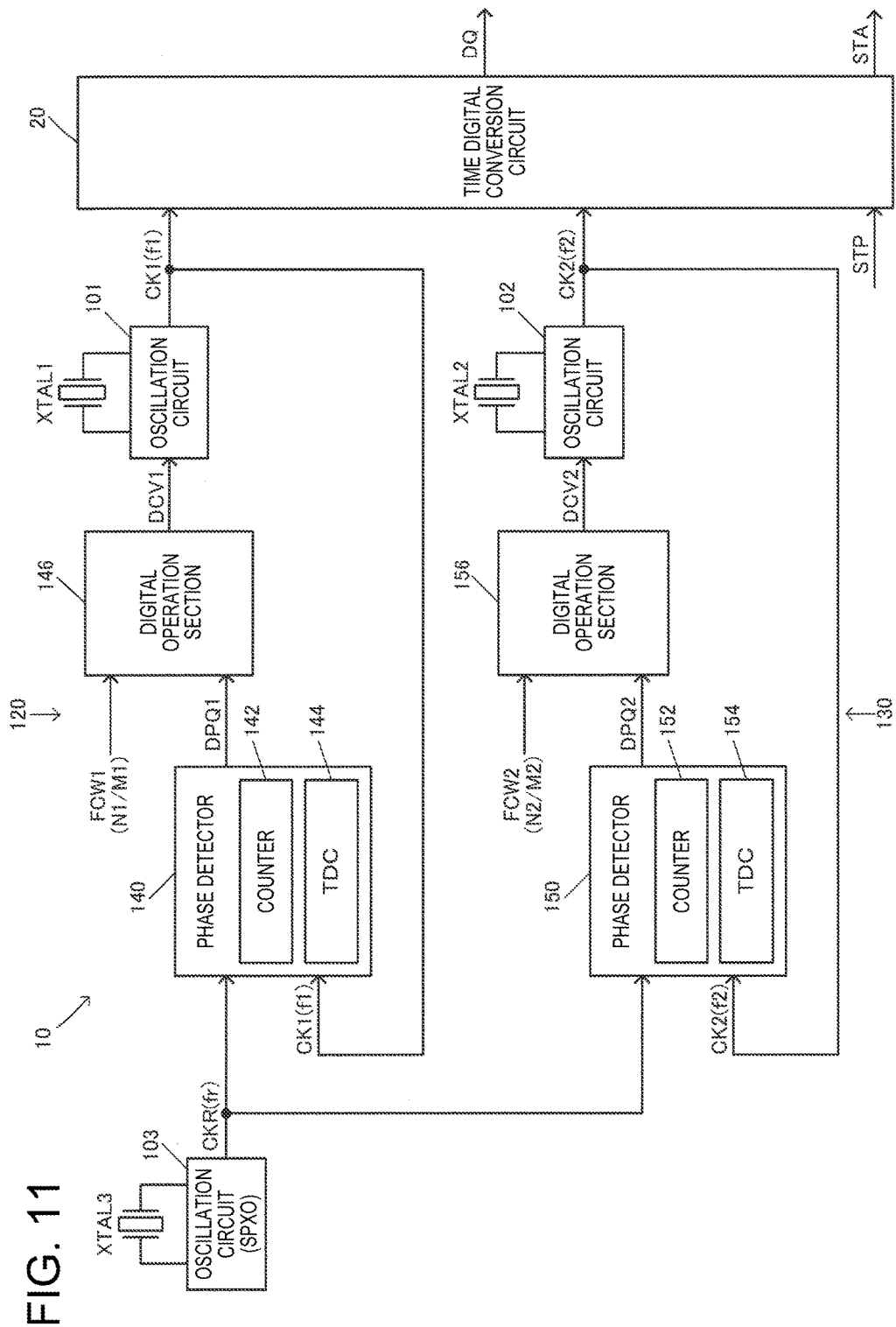
FIG. 11 is a diagram showing a detailed second configuration example of the circuit device according to the embodiment.

Further, the PLL circuit 120 of the present embodiment includes the phase detector 126 (140) for performing the phase comparison between the clock signal CK1 or a signal based on the clock signal CK1, and the reference clock signal CKR or a signal based on the reference clock signal CKR. For example, the phase detector 126 shown in FIG. 5 performs the phase comparison between the frequency-divided clock signal DCK1 as the signal based on the clock signal CK1, and the frequency-divided clock signal DCK2 as the signal based on the reference clock signal CKR. The phase detector 140 shown in FIG. 11 described later performs the phase comparison between the clock signal CK1 and the reference clock signal CKR. Further, the phase detectors 126, 140 each output the signal of the phase comparison result to a circuit in the posterior stage. In FIG. 5, the phase detector 126 outputs the analog signal PQ1 as the up/down signal to the charge pump circuit 128 in the posterior stage. In FIG. 11 described later, the phase detector 140 outputs the digital data DPQ1 to a digital operation section 146 in the posterior stage.

Further, the PLL circuit 130 of the present embodiment includes the phase detector 136 (150) for performing the phase comparison between the clock signal CK2 or a signal based on the clock signal CK2, and the reference clock signal CKR or a signal based on the reference clock signal CKR. For example, the phase detector 136 shown in FIG. 5 performs the phase comparison between the frequency-divided clock signal DCK3 as the signal based on the clock signal CK2, and the frequency-divided clock signal DCK4 as the signal based on the reference clock signal CKR. The phase detector 150 shown in FIG. 11 described later performs the phase comparison between the clock signal CK2 and the reference clock signal CKR. Further, the phase detectors 136, 150 each output the signal of the phase comparison result to a circuit in the posterior stage. In FIG. 5, the phase detector 136 outputs the analog signal PQ2 as the up/down signal to the charge pump circuit 138 in the posterior stage. In FIG. 11 described later, the phase detector 150 outputs the digital data DPQ2 to a digital operation section 156 in the posterior stage.

By providing such phase detectors 126, 136 (140, 150), it is possible to realize the control of feeding back the phase comparison result between the clock signal CK1 or the signal based on the clock signal CK1 and the reference clock signal CKR or the signal based on the reference clock signal CKR, and the control of feeding back the phase comparison result between the clock signal CK2 or the signal based on the clock signal CK2 and the reference clock signal CKR or the signal based on the reference clock signal CKR. Thus, it becomes possible to realize the phase synchronization for making the transition timings of the clock signals CK1, CK2 coincide with each other at the phase synchronization timing.

Further, in FIG. 5, the PLL circuit 120 has the frequency divider circuit 122 for dividing the frequency of the clock signal CK1 to output the frequency-divided clock signal DCK1 to the phase detector 126, and the frequency divider circuit 124 for dividing the frequency of the reference clock signal CKR to output the frequency-divided clock signal DCK2 to the phase detector 126. Further, the PLL circuit 130 has the frequency divider circuit 132 for dividing the frequency of the clock signal CK2 to output the frequency-divided clock signal DCK3 to the phase detector 136, and the frequency divider circuit 134 for dividing the frequency of the reference clock signal CKR to output the frequency-divided clock signal DCK4 to the phase detector 136.

As described above, by providing the frequency divider circuits 122, 124 to the PLL circuit 120, it becomes possible to perform the control of feeding back the phase comparison result between the frequency-divided clock signals DCK1, DCK2 in the phase detector 126 to realize the phase synchronization between the clock signal CK1 and the reference clock CKR. Further, by providing the frequency divider circuits 132, 134 to the PLL circuit 130, it becomes possible to perform the control of feeding back the phase comparison result between the frequency-divided clock signals DCK3, DCK4 in the phase detector 136 to realize the phase synchronization between the clock signal CK2 and the reference clock CKR. Further, by performing the phase synchronization between the clock signal CK1 and the reference clock signal CKR and the phase synchronization between the clock signal CK2 and the reference clock signal CKR, it becomes possible to realize the phase synchronization between the clock signals CK1, CK2.

Specifically, in FIG. 5, the frequency divider circuit 122 divides the frequency of the clock signal CK1, and the frequency divider circuit 124 divides the frequency of the reference clock signal CKR so as to achieve N1/f1=M1/fr. For example, the frequency divider circuit 122 performs the frequency division for reducing the clock frequency f1 to 1/N1, and the frequency divider circuit 124 performs the frequency division for reducing the clock frequency fr to 1/M1. Then, by performing the feedback control for making the transition timings of the frequency-divided clock signals DCK1, DCK2 obtained by the frequency division coincide with each other, the relationship of N1/f1=M1/fr becomes to be fulfilled as shown in FIG. 6. Further, in FIG. 5, the frequency divider circuit 132 divides the frequency of the clock signal CK2, and the frequency divider circuit 134 divides the frequency of the reference clock signal CKR so as to achieve N2/f2=M2/fr. For example, the frequency divider circuit 132 performs the frequency division for reducing the clock frequency f2 to 1/N2, and the frequency divider circuit 134 performs the frequency division for reducing the clock frequency fr to 1/M2. Then, by performing the feedback control for making the transition timings of the frequency-divided clock signals DCK3, DCK4 obtained by the frequency division coincide with each other, the relationship of N2/f2=M2/fr becomes to be fulfilled as shown in FIG. 7. Thus, the phase synchronization at an appropriate timing becomes possible, and it is possible to prevent occurrence of a trouble caused by the phase synchronization at an inappropriate phase synchronization timing, and so on. Specifically, the process of the time-to-digital conversion using the period TAB as the processing period becomes possible.

Further, as shown in FIG. 5, the circuit device 10 according to the present embodiment includes the oscillation circuit 101, which is controlled based on the phase comparison result of the phase detector 126, and oscillates the resonator XTAL1 to generate the clock signal CK1. For example, the charge pump circuit 128 performs the charge pump operation based on the signal PQ1 (the up/down signal) of the phase comparison result from the phase detector 126, and the oscillation circuit 101 generates the clock signal CK1 based on the control voltage VC1 generated by the charge pump operation. Further, the circuit device 10 includes the oscillation circuit 102, which is controlled based on the phase comparison result of the phase detector 136, and oscillates the resonator XTAL2 to generate the clock signal CK2. For example, the charge pump circuit 138 performs the charge pump operation based on the signal PQ2 (the up/down signal) of the phase comparison result from the phase detector 136, and the oscillation circuit 102 generates the clock signal CK2 based on the control voltage VC2 generated by the charge pump operation.

By adopting this process, it becomes possible to adjust the clock frequencies f1, f2 of the clock signals CK1, CK2 based on the phase comparison result in the phase detectors 126, 136 to thereby realize the phase synchronization between the clock signals CK1, CK2 which satisfies, for example, the relationship of N/f1=M/f2. By realizing such phase synchronization, it becomes possible to achieve the simplification of the process and the circuit configuration of the time-to-digital conversion, and the improvement in performance (e.g., increase in accuracy) of the process of the time-to-digital conversion.

By generating the clock signals CK1, CK2 using the resonators XTAL1, XTAL2 as described above, and then performing the time-to-digital conversion using these clock signals CK1, CK2, the improvement in accuracy and so on of the time-to-digital conversion can be achieved. Further, if the reference clock signal CKR is also generated using the resonator XTAL3, further improvement in accuracy of the time-to-digital conversion and so on can be achieved. In particular, it becomes possible to significantly improve the accuracy of the time-to-digital conversion compared to the related art method of realizing the time-to-digital conversion using the delay elements as the semiconductor elements.

3. Second Configuration Example

FIG. 11 shows a second configuration example of the circuit device 10 according to the present embodiment. The second configuration example shown in FIG. 11 is different in circuit configuration of the PLL circuits 120, 130 compared to the first configuration example shown in FIG. 5. For example, in contrast to the fact that the PLL circuits 120, 130 shown in FIG. 5 each have an analog type circuit configuration, the PLL circuits 120, 130 shown in FIG. 11 each have a digital type (ADPLL) circuit configuration.

The PLL circuit 120 shown in FIG. 11 includes the phase detector 140, and the digital operation section 146. Further, the oscillation circuit 101 is formed as a digitally controlled oscillation circuit (DCXO) the oscillation frequency of which is controlled based on the frequency control data DCV1.

The phase detector 140 is a circuit for performing the phase comparison between the clock signal CK1 (a feedback signal) from the oscillation circuit 101 and the reference clock signal CKR from the oscillation circuit 103 in a digital manner. The phase detector 140 includes a counter 142 and a TDC 144 (time-to-digital converter). The counter 142 generates the digital data corresponding to the integral part of the result obtained by dividing the clock frequency fr (the reference frequency) of the reference clock signal CKR by the clock frequency f1 of the clock signal CK1. The TDC 144 generates the digital data corresponding to a fractional part of the division result. The data corresponding to the addition result of the integral part and the fractional part is output as the digital data DPQ1. Here, the TDC 144 can be constituted by, for example, a plurality of delay elements, a plurality of latch circuits, and a logic circuit for generating the digital data corresponding to the fractional part of the division result based on the output signal of the plurality of latch circuits.

The digital operation section 146 detects the phase error with preset frequency data FCW1 based on the preset frequency data FCW1 and the digital data DPQ1 of the comparison result from the phase detector 140. Then, by performing a smoothing process of the phase error, the digital operation section 146 generates the frequency control data DCV1, and then outputs the frequency control data DCV1 to the oscillation circuit 101. The oscillation circuit 101 is controlled in oscillation frequency based on the frequency control data DCV1 to generate the clock signal CK1. Then, the clock signal CK1 thus generated is fed back to the phase detector 140.

Further, the PLL circuit 130 shown in FIG. 11 includes the phase detector 150, and the digital operation section 156. Further, the oscillation circuit 102 is formed as a digitally controlled oscillation circuit (DCXO) the oscillation frequency of which is controlled based on the frequency control data DCV2.

The phase detector 150 is a circuit for performing the phase comparison between the clock signal CK2 from the oscillation circuit 102 and the reference clock signal CKR from the oscillation circuit 103 in a digital manner. The phase detector 150 includes a counter 152 and a TDC 154. The counter 152 generates the digital data corresponding to the integral part of the result obtained by dividing the clock frequency fr of the reference clock signal CKR by the clock frequency f2 of the clock signal CK2. The TDC 154 generates the digital data corresponding to a fractional part of the division result. The data corresponding to the addition result of the integral part and the fractional part is output as the digital data DPQ2.

The digital operation section 156 detects the phase error with preset frequency data FCW2 based on the preset frequency data FCW2 and the digital data DPQ2 of the comparison result from the phase detector 150. Then, by performing a smoothing process of the phase error, the digital operation section 156 generates the frequency control data DCV2, and then outputs the frequency control data DCV2 to the oscillation circuit 102. The oscillation circuit 102 is controlled in oscillation frequency based on the frequency control data DCV2 to generate the clock signal CK2. Then, the clock signal CK2 thus generated is fed back to the phase detector 150.

In the PLL circuit 120 shown in FIG. 11, the frequency control data DCV1 is generated so that the relationship of f1=FCW1×fr becomes true to control the oscillation frequency of the oscillation circuit 101. Therefore, in order to arrange that the relationship of N1/f1=M1/fr is fulfilled as shown in FIG. 6 described above, it is sufficient to set the preset frequency data to, for example, FCW1=N1/M1. By adopting this configuration, the frequency control data DCV1 is generated so as to fulfill FCW1=N1/M1=f1/fr, and thus, the relationship of N1/f1=M1/fr becomes to be fulfilled.

Further, in the PLL circuit 130, the frequency control data DCV2 is generated so that the relationship of f2=FCW2×fr becomes true to control the oscillation frequency of the oscillation circuit 102. Therefore, in order to arrange that the relationship of N2/f2=M2/fr is fulfilled as shown in FIG. 7 described above, it is sufficient to set the preset frequency data to, for example, FCW2=N2/M2. By adopting this configuration, the frequency control data DCV2 is generated so as to fulfill FCW2=N2/M2=f21/fr, and thus, the relationship of N2/f2=M2/fr becomes to be fulfilled.

It should be noted that the configuration of the PLL circuits 120, 130 of the digital type is not limited to the configuration shown in FIG. 11, but a variety of practical modifications can be adopted. For example, it is also possible to realize the digital type PLL circuits 120, 130 with the configuration using a Bang-Bang type phase detector and PI control instead of using the TDC 144, 154.

4. Oscillation Circuit

FIG. 12 shows a first configuration example of the oscillation circuit 100. Here, on behalf of the oscillation circuits 101, 102, the description of oscillation circuit 100 is used.

The oscillation circuit 100 (101, 102) shown in FIG. 12 includes a buffer circuit BAB for oscillation, the variable capacitance circuits CB1, CB2 (variable capacitors, capacitors in a broad sense), and a feedback resistor RB. The buffer circuit BAB can be formed of one inverter circuit or a plurality of stages (odd stages) of inverter circuits. In FIG. 12, the buffer circuit BAB is constituted by three stages of inverter circuits IV1, IV2, and IV3. The buffer circuit BAB (IV1 through IV3) can also be a circuit capable of the control of enabling/disabling the oscillation, and the control of the current flowing through the buffer circuit BAB.

One end (NB1) and the other end (NB2) of the resonator XTAL are respectively provided with variable capacitance circuits CB1, CB2. Further, between the one end and the other end of the resonator XTAL, there is disposed the feedback resistor RB. The capacitance values of the variable capacitance circuits CB1, CB2 are controlled based on the control voltages VC1, VC2 (control signals in a broad sense), respectively. The variable capacitance circuits CB1, CB2 are each realized by a variable capacitance diode (varactor) or the like. By controlling the capacitance value in such a manner, it becomes possible to adjust (fine adjust) the oscillation frequency (the clock frequency) of the oscillation circuit 100.

It should be noted that it is also possible to provide the variable capacitance circuit to only either one of the one end and the other end of the resonator XTAL. Further, it is also possible to provide an ordinary capacitor with an invariable capacitance value instead of the variable capacitance circuit.

FIG. 13 shows a second configuration example of the oscillation circuit 100. The oscillation circuit 100 has a current source IBX, a bipolar transistor TRX, a resistor RX, capacitors CX2, CX3, and a variable capacitance circuit CX1 (a variable capacitor). For example, the current source IBX, the bipolar transistor TRX, the resistor RX, and the capacitor CX3 constitute a buffer circuit BAX for the oscillation.

The current source IBX supplies the collector of the bipolar transistor TRX with a bias current. The resistor RX is disposed between the collector and the base of the bipolar transistor TRX.

One end of the variable capacitance circuit CX1 having a variable capacitance is connected to one end (NX1) of the resonator XTAL. Specifically, the one end of the variable capacitance circuit CX1 is connected to the one end of the resonator XTAL via a first terminal (an resonator pad) for the resonator of the circuit device 10. One end of the capacitor CX2 is connected to the other end (NX2) of the resonator XTAL. Specifically, the one end of the capacitor CX2 is connected to the other end of the resonator XTAL via a second terminal (an resonator pad) for the resonator of the circuit device 10. One end of the capacitor CX3 is connected to the one end of the resonator XTAL, and the other end of the capacitor CX3 is connected to the collector of the bipolar transistor TRX.

The base-emitter current generated by the oscillation of the resonator XTAL flows through the bipolar transistor TRX. Further, when the base-emitter current increases, the collector-emitter current of the bipolar transistor TRX increases, and the bias current branched from the current source IBX to the resistor RX decreases, and therefore, the collector voltage VCX is lowered. In contrast, when the base-emitter current of the bipolar transistor TRX decreases, the collector-emitter current decreases, and the bias current branched from the current source IBX to the resistor RX increases, and therefore, the collector voltage VCX is raised. The collector voltage VCX is fed back to the one end of the resonator XTAL via the capacitor CX3. Therefore, the AC component is cut by the capacitor CX3, and the DC component is fed back. The buffer circuit BAX for the oscillation constituted by the bipolar transistor TRX and so on as described above acts as an inverting circuit (an inverting amplifier circuit) for outputting an inversion signal (a signal with a phase difference of 180 degrees) of the signal of the node NX2 to the node NX1.

The capacitance value of the variable capacitance circuit CX1 formed of the variable capacitance diode (varactor) or the like is controlled based on the control voltage VC (the control signal). Thus, the adjustment of the oscillation frequency of the oscillation circuit 100 becomes possible. For example, in the case in which the oscillation frequency of the resonator XTAL has temperature dependency, the temperature compensation and so on of the oscillation frequency also becomes possible.

It should be noted that the configuration of the oscillation circuit 100 (101, 102) is not limited to the configuration shown in FIG. 12 and FIG. 13, but a variety of practical modifications can be adopted. For example, as the configuration of the buffer circuit, and the connection configuration of the variable capacitance circuit and the capacitors, there can be adopted a variety of configurations. For example, it is possible to arrange that the capacitance value of each of the variable capacitance circuits (CB1, CB2, and CX1) can be adjusted with a digital value. In this case, the variable capacitance circuit is constituted by a plurality of capacitors (a capacitor array), and a plurality of switch elements (a switch array) each controlled to be set to the ON state or the OFF state based on the frequency control data (a control signal in a broad sense) as the digital value. Each of the switch elements is electrically connected to corresponding one of the capacitors. Further, by setting each of the switch elements to the ON state or the OFF state, the number of capacitors, one ends of which are connected to the one end of the resonator XTAL out of the plurality of capacitors, varies. Thus, the capacitance value of the variable capacitance circuit is controlled, and thus, the capacitance value of the one end of the resonator XTAL changes. Therefore, the capacitance value of the variable capacitance circuit is directly controlled by the frequency control data, and it becomes possible to control the oscillation frequency of the oscillation signal.

5. Configuration of Time-to-Digital Conversion Circuit

Figure 14:
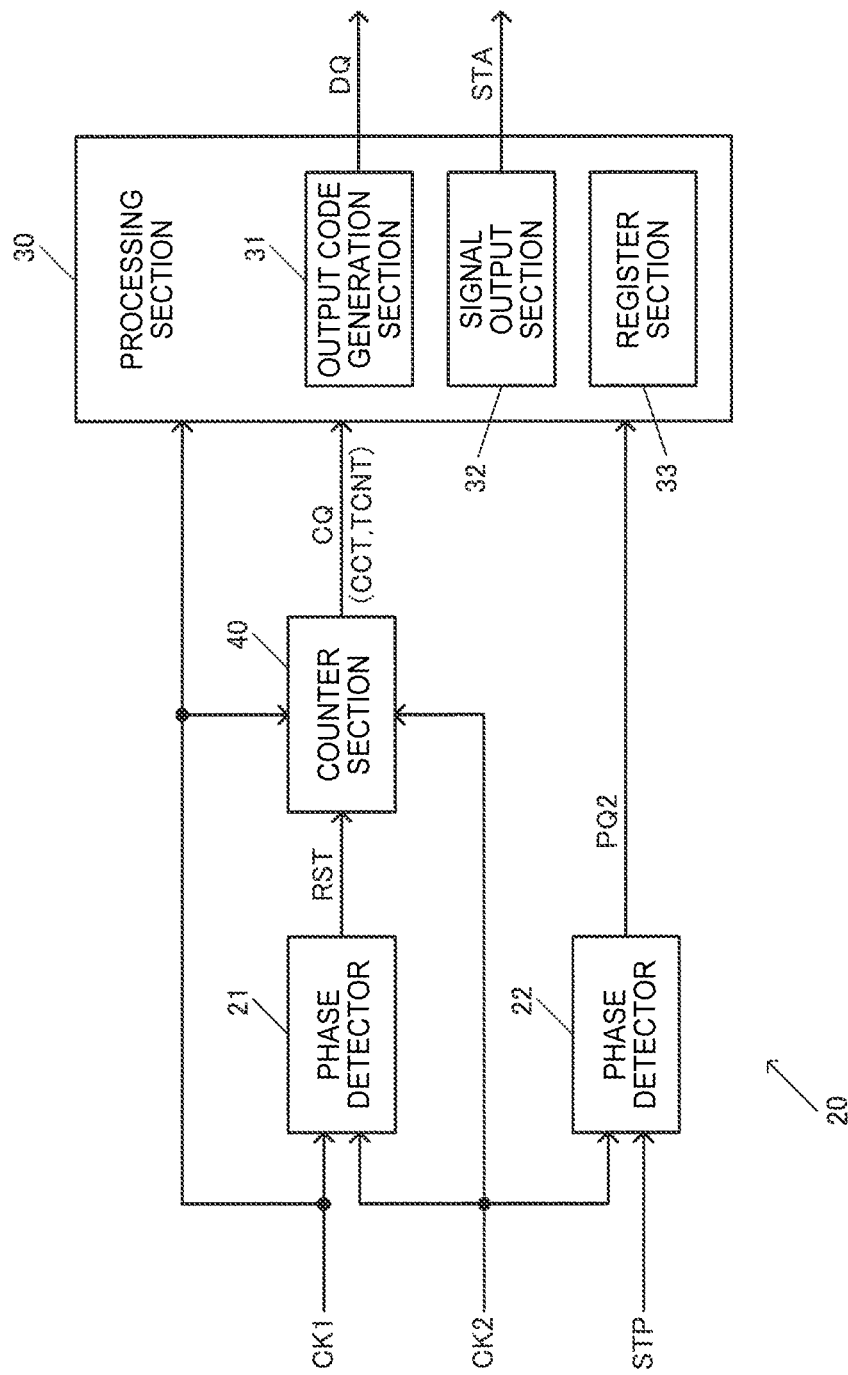
FIG. 14 is a diagram showing a configuration example of a time-to-digital conversion circuit.

FIG. 14 shows a configuration example of the time-to-digital conversion circuit 20. The time-to-digital conversion circuit 20 includes phase detectors 21, 22, a processing section 30, and a counter section 40. It should be noted that the configuration of the time-to-digital conversion circuit 20 is not limited to the configuration shown in FIG. 14, but it is possible to adopt a variety of practical modifications such as elimination of some of the constituents or addition of other constituents.

The clock signals CK1, CK2 are input to the phase detector 21 (a phase comparator), and the phase detector 21 outputs a reset signal RST to the counter section 40. For example, the phase detector 21 outputs the reset signal RST, which is a pulse signal activated at the phase synchronization timing.

The signal STP and the clock signal CK2 are input to the phase detector 22 (a phase comparator), and the phase detector 22 outputs the signal PQ2 as the phase comparison result. The phase detector 22 samples, for example, one of the signal STP and the clock signal CK2 with the other thereof to thereby perform the phase comparison between the signal STP and the clock signal CK2. The signal PQ2 as the phase comparison result is output to the processing section 30.

The counter section 40 performs a counting process of a count value. For example, the counter section 40 includes at least one of a first counter for performing the counting process based on the clock signal CK1, and a second counter for performing the counting process based on the clock signal CK2. The count value of each of the first and second counters is reset based on the reset signal RST from, for example, the phase detector 22. Further, the count value CQ in the counter section 40 is output to the processing section 30. The count value CQ is the count value of at least one of the first and second counters for performing the counting operation base on the clock signals CK1, CK2, respectively, and corresponds to CCT, TCNT, and so on described later.

The processing section 30 performs the process of converting the time into the digital value DQ. In other words, the processing section 30 performs a variety of types of arithmetic processing related to the time-to-digital conversion. For example, the processing section 30 performs the arithmetic processing for obtaining the digital value DQ corresponding to the time difference between the signal STA and the signal STP. Specifically, the processing section 30 performs the arithmetic processing of the time-to-digital conversion based on the count value CQ from the counter section 40 and the signal PQ2 as the phase comparison result from the phase detector 22. The processing section 30 can be realized by a logic circuit such as an ASIC, a processor such as a CPU, and so on.

The processing section 30 includes an output code generation section 31, a signal output section 32, and a register section 33. The output code generation section 31 performs the arithmetic processing of the time-to-digital conversion to output the conclusive digital value DQ as a conclusive output code. The signal output section 32 generates and then outputs the signal STA. The signal output section 32 outputs the signal STA based on the clock signal CK1. For example, the signal output section 32 outputs the signal STA based on, for example, the clock signal CK1 in every clock cycle of the clock signal CK1 as described later. Alternatively, the signal output section 32 outputs the signal STA with the clock cycle designated by, for example, the clock cycle designation value. The register section 33 can be formed of a single register or a plurality of registers. For example, the register section 33 includes a register for storing clock cycle designation information described later, and so on. The register section 33 can be realized by, for example, flip-flop circuits or memory elements.

Figure 15:
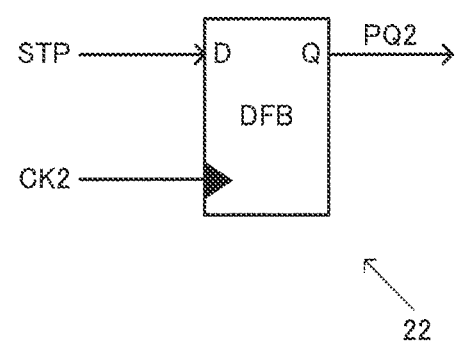
FIG. 15 is a diagram showing a configuration example of a phase detector.

FIG. 15 shows a configuration example of the phase detector 22. The phase detector 22 is formed of, for example, a flip-flop circuit DFB. The signal STP is input to the data terminal of the flip-flop circuit DFB, and the clock signal CK2 is input to the clock terminal thereof. Thus, the phase comparison achieved by sampling the signal STP with the clock signal CK2 can be realized. It should be noted that it is also possible to arrange that the clock signal CK2 is input to the data terminal of the flip-flop circuit DFB, and the signal STP is input to the clock terminal thereof. Thus, the phase comparison achieved by sampling the clock signal CK2 with the signal STP can be realized.

6. Repeating Method of Signal STA

Then, a variety of examples of the time-to-digital conversion method of the present embodiment will be described. Firstly, a method of repeatedly generating the signal STA in every clock cycle will be described.

Figure 16:
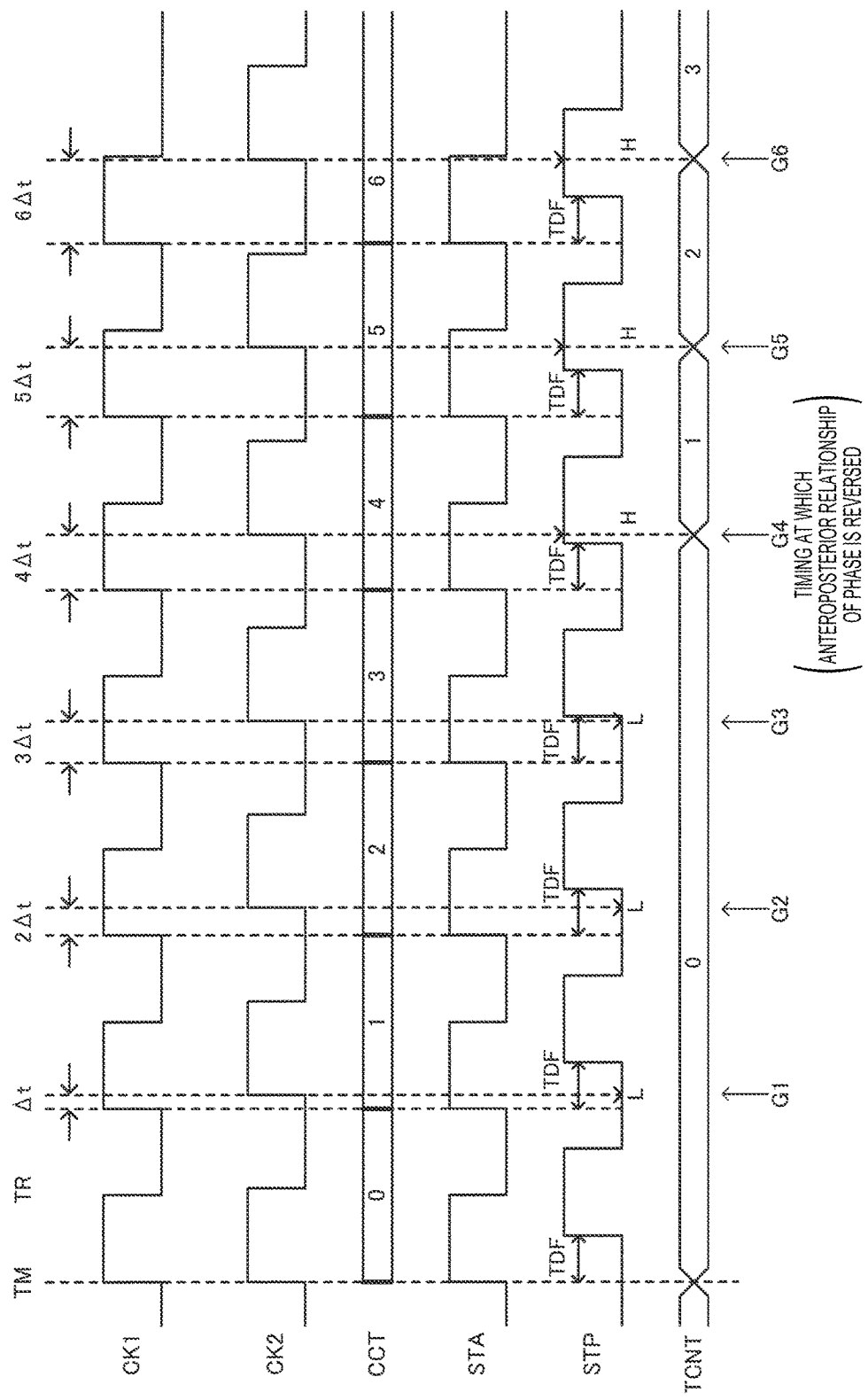
FIG. 16 is a signal waveform chart for explaining the repeating method of the signal STA.

FIG. 16 is a signal waveform chart for explaining the repeating method of the signal SAT (hereinafter arbitrarily described simply as a repeating method) of the present embodiment. In FIG. 16, the phase synchronization between the clock signals CK1, CK2 is achieved at the phase synchronization timing TM. Specifically, at the phase synchronization timing TM, there is performed the phase synchronization for making the transition timings (e.g., rising transition timings, rising edges) of the clock signals CK1, CK2 coincide with each other. The phase synchronization is achieved by the PLL circuits 120, 130 shown in FIG. 1. At the phase synchronization timing TM, the count value TCNT of the counter section 40 (the second counter) is reset to, for example, 0.

It should be noted that in the case in which the phase synchronization timing TM is a known timing in the system of the circuit device 10, the phase synchronization timing TM is set by, for example, a timing control section (not shown). In this case, it results that the function of the phase detector 21 shown in FIG. 14 is realized by the timing control section. Specifically, the timing control section outputs the reset signal RST, which is activated at the phase synchronization timing TM, to the counter section 40.

Then, after the phase synchronization timing TM between the clock signals CK1, CK2, the time-to-digital conversion circuit 20 makes the transition of the signal level of the signal STA based on the clock signal CK1. Specifically, after the phase synchronization timing TM, the time-to-digital conversion circuit 20 makes the transition of the signal level of the signal STA at every clock cycle of the clock signal CK1. For example, by the signal output section 32 shown in FIG. 14 outputting the signal obtained by buffering the clock signal CK1 with a buffering circuit as the signal STA, the signal level of the signal STA becomes to make the transition at every clock cycle.

In FIG. 16, CCT denotes a clock cycle value. The clock cycle value CCT is updated at every clock cycle of the clock signal CK1. Specifically, the clock cycle value CCT is incremented at every clock cycle. It should be noted that the clock cycle value of the first clock cycle is set to CCT=0 here for the sake of convenience of explanation. Therefore, the clock cycle value of the subsequent clock cycle becomes CCT=1. Further, although in FIG. 16, CCT denotes the clock cycle value of the clock signal CK1, it is also possible to use the clock cycle value of the clock signal CK2.

As described above, when the signal STA makes the transition of the signal level based on the clock signal CK1 after the phase synchronization timing TM, the signal STP makes the transition of the signal level in accordance with the signal STA as explained with reference to FIG. 3 and FIG. 4. Here, the time difference in transition timing between the signals STA, STP is defined as TDF.

In this case, the time-to-digital conversion circuit 20 performs the phase comparison between the signal STP and the clock signal CK2 as indicated by the arrows G1 through G6 shown in FIG. 16. Then, based on the result of the phase comparison, the time-to-digital conversion circuit 20 obtains the digital value DQ corresponding to the time difference TDF in transition timing between the signals STA, STP. Specifically, the processing section 30 shown in FIG. 14 performs the arithmetic processing for obtaining the digital value DQ based on the signal PQ2 as the phase comparison result from the phase detector 22.

For example, as explained with reference to FIG. 2, after the phase synchronization timing TM, the inter-clock time difference TR as the time difference in transition timing between the clock signals CK1, CK2 continues to increase at every clock cycle of the clock signal CK1 in such a manner as $\Delta t, 2\times\Delta t, 3\times\Delta t, \ldots 6\times\Delta t$. In the repeating method of the present embodiment, the time-to-digital conversion is realized focusing attention on the inter-clock time difference TR increasing by $\Delta t$ in such a manner after the phase synchronization timing TM.

Specifically, the time-to-digital conversion circuit 20 performs the phase comparison between the signal STP and the clock signal CK2 at every clock cycle as indicated by the arrows G1 through G6 shown in FIG. 16. The phase comparison can be realized by sampling, for example, one of the signal STP and the clock signal CK2 with the other thereof.

Further, at the arrows G1 through G3 shown in FIG. 16, the signal PQ2 as the phase comparison result, which is the signal obtained by sampling the signal STP with the clock signal CK2, is set to the L level. In other words, at the arrows G1 through G3, since the signal STP lags in phase behind the clock signal CK2, the signal PQ2 is set to the L level.

As described above, at the arrows G1 through G3 shown in FIG. 16, based on the result of the phase comparison between the signal STP and the clock CK2, it is determined that the signal STP lags in phase behind the clock signal CK2. In other words, at the arrows G1, G2, and G3, TDF>TR=Δt, TDF>TR=2×Δt, and TDF>TR=3×Δt are true, respectively, and the time difference TDF in transition timing between the signals STA, STP is made longer than the inter-clock time difference TR between the clock signals CK1, CK2.

Further, at the arrow G4 shown in FIG. 16, the anteroposterior relationship in phase between the signal STP and the clock signal CK2 is reversed. For example, the state in which the signal STP lags in phase behind the clock signal CK2 is switched to the state in which the signal STP leads in phase over the clock signal CK2.

When the anteroposterior relationship between the phases is reversed in such a manner, the signal PQ2 as the phase comparison result which is the signal obtained by sampling the signal STP with the clock signal CK2 turns to the H level as indicated by the arrows G4 through G6. In other words, at the arrows G4 through G6, since the signal STP leads in phase over the clock signal CK2, the signal PQ2 is set to the H level.

As described above, at the arrows G4 through G6, based on the result of the phase comparison between the signal STP and the clock signal CK2, it is determined that the signal STP leads in phase over the clock signal CK2. In other words, at the arrows G4, G5, and G6, TDF<TR=4×Δt, TDF<TR=5×Δt, and TDF<TR=6×Δt are true, respectively, and the time difference TDF in transition timing between the signals STA, STP is shorter than the inter-clock time difference TR between the clock signals CK1, CK2.

Further, at the arrows G1 through G3 shown in FIG. 16, the signal PQ2 as the phase comparison result is in the L level, and it is determined that the signal STP lags in phase behind the clock signal CK2. In this case, the count value TCNT is not updated. For example, the count value TCNT does not increase from 0. In contrast, at the arrows G4 through G6, the signal PQ2 as the phase comparison result is in the H level, and it is determined that the signal STP leads in phase over the clock signal CK2. In this case, the count value TCNT is updated. For example, the count value TCNT is incremented by 1, for example, at every clock cycle.

The time-to-digital conversion circuit 20 (the processing section 30) obtains the digital value DQ corresponding to the time difference TDF using the count value TCNT obtained in such a manner. For example, by performing the conversion process of a code represented by the count value TCNT, the output code as the conclusive digital value DQ is obtained and then output.

Figure 17:
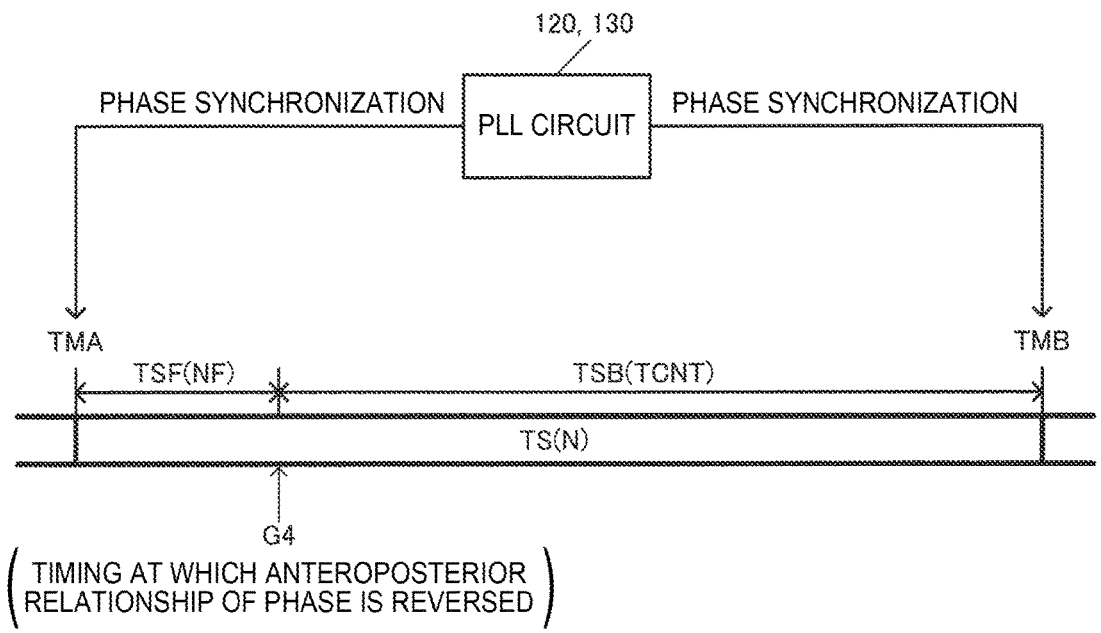
FIG. 17 is a signal waveform chart for explaining the repeating method of the signal STA.

FIG. 17 is an explanatory diagram of the repeating method of the present embodiment. At the phase synchronization timings TMA, TMB, the phase synchronization between the clock signals CK1, CK2 is performed by the PLL circuits 120, 130. Thus, the transition timings of the clock signals CK1, CK2 become to coincide with each other at the phase synchronization timings TMA, TMB. Further, the period between the phase synchronization timings TMA, TMB is defined as the measurement period TS. In the repeating method of the present embodiment, the digital value DQ corresponding to the time difference TDF is obtained in the measurement period TS.

Specifically, as indicated by the arrow G4 shown in FIG. 16 and FIG. 17, the time-to-digital conversion circuit 20 identifies the timing (the clock cycle) at which the anteroposterior relationship in phase between the signal STP and the clock signal CK2 is reversed, to thereby obtain the digital value DQ corresponding to the time difference TDF. For example, by identifying the clock cycle which is indicated by the arrow G4, and in which CCT=4 is obtained, it can be determined that the digital value DQ corresponding to the time difference TDF is the digital value (or the digital value corresponding to a value between 3×Δt and 4×Δt) corresponding to, for example, TR=4×Δt. Therefore, since it becomes possible to convert the time difference TDF into the digital value DQ in a single measurement period TS shown in FIG. 17, speeding-up of the time-to-digital conversion can be achieved.

For example, in the related art method of Document 4 described above, since just one start pulse is generated during one measurement period for performing the time measurement, it is necessary to repeat the measurement period an extremely large number of times in order to obtain the conclusive digital value.

In contrast, according to the repeating method of the present embodiment, the digital value DQ is obtained by generating the signal STA a plurality of times to perform the phase comparison a plurality of times in one measurement period TS as shown in FIG. 16 and FIG. 17. Thus, it becomes possible to obtain the conclusive digital value DQ within the single measurement period TS, and therefore, it is possible to dramatically speed-up the time-to-digital conversion compared to the related art method.

It should be noted that in FIG. 17, the length of the measurement period TS corresponds to, for example, the number of clock pulses N (the number of clock cycles) of the clock signal CK1 in the measurement period TS. For example, the phase synchronization between the clock signals CK1, CK2 is performed in every measurement period TS corresponding to the preset number of clock pulses N as a result. Further, in the repeating method of the present embodiment, in order to realize the high-resolution time-to-digital conversion, the number of clock pulses N in the measurement period TS is set to an extremely large number such as 1,000 or more (or 5,000 or more). For example, in the case of defining the clock frequencies of the clock signals CK1, CK2 as f1, f2, the resolution Δt of the time-to-digital conversion of the present embodiment can be expressed as Δt=|f1−f2|/(f1×f2). Therefore, the smaller the frequency difference |f1−f2| is, or the larger the value of f1×f2 is, the finer the resolution Δt becomes, and thus, the time-to-digital conversion high in resolution can be realized. Further, as the resolution Δt becomes finer, the number of clock pulses N in the measurement period TS also increases.

Further, the count value TCNT corresponds to the length of the period TSB shown in FIG. 17. Here, the anterior period from the phase synchronization timing TMA to the timing indicated by the arrow G4 at which anteroposterior relationship in phase is reversed is defined as TSF, and the posterior period from the timing of the arrow G4 to the phase synchronization timing TMB is defined as TSB. For example, in the case of defining the number of clock pulses (the number of clock cycles) of the clock signal CK1 in the period TSF as NF, N=NF+TCNT, for example, is true. For example, in FIG. 16, since NF=4 is assumed, the value corresponding to the conclusive digital value DQ=4×Δt becomes a digital value corresponding to the number of clock pulses NF. Therefore, as a result, the time-to-digital conversion circuit 20 (the processing section 30) obtains the digital value corresponding to NF=N−TCNT based on the count value TCNT. For example, in the case in which the digital value DQ is an 8-bit value, the digital value corresponding to the number of clock pulses N becomes, for example, 11111111. It should be noted that it is also possible to perform the count process of the number of clock pulses NF to thereby obtain the digital value DQ.

It should be noted that in the case of increasing the number of clock pulses N corresponding to the measurement period TS, the measurable time difference TDF in FIG. 16 decreases, and therefore, the dynamic range reduces. However, in the repeating method of the present embodiment, the time-to-digital conversion is completed in one measurement period TS while increasing the number of clock pulses N to improve the resolution. Thus, it becomes possible to realize an increase in resolution while achieving the speeding-up of the conversion process as in the case of, for example, the flash A/D conversion.

In this case, in the repeating method of the present embodiment, it is also possible to arrange that the signal STA is generated only in a specific period to perform the phase comparison instead of always generating the signal STA at every clock cycle to perform the phase comparison. For example, it is also possible to arrange that the search range of the digital value DQ is narrowed by the method of binary search described later, and then the signal STA is generated to perform the phase comparison at every clock cycle in the period corresponding to the search range to thereby obtain the conclusive digital value DQ. In this case, it is sufficient to perform the time-to-digital conversion in which the signal STA is generated at every clock cycle to perform the phase comparison only in the period corresponding to the narrowed search range in, for example, the measurement period TS shown in FIG. 17. Further, after the timing (G4) at which the anteroposterior relationship in phase is reversed is identified, it is possible to stop generating the signal STA to thereby achieve reduction of power consumption.

Further, in the present embodiment, as shown in FIG. 1, the clock signals CK1, CK2 are made to be clock signals generated using the resonators XTAL1, XTAL2, respectively. As described above, according to the method of using the clock signals CK1, CK2 generated using the resonators XTAL1, XTAL2, the accuracy of the measurement of the time (the physical quantity) can dramatically be improved compared to the related art method of realizing the time-to-digital conversion using a semiconductor element as in the vernier delay circuit.

For example, in the related art method using the semiconductor element, there is a problem that it is difficult to improve the accuracy although it is relatively easy to improve the resolution. Specifically, the delay time of the delay element as the semiconductor element significantly varies due to the manufacturing variation and the environmental variation. Therefore, due to the variation, there is a limitation in improvement of the measurement accuracy. For example, it is possible to guarantee the relative accuracy to some extent, but it is difficult to guarantee the absolute accuracy.

In contrast, the oscillation frequency of the resonator is extremely small in variation due to the manufacturing variation and the environmental variation compared to the delay time of the delay element as the semiconductor element. Therefore, according to the method of performing the time-to-digital conversion using the clock signals CK1, CK2 generated using the resonators XTAL1, XTAL2, the accuracy can dramatically be improved compared to the related art method of using the semiconductor element. Further, by decreasing the frequency difference between the clock signals CK1, CK2, it is also possible to improve the resolution.

For example, by setting the frequency difference $\Delta f$ between the clock signals CK1, CK2 to $\Delta f=|f1-f2|=1$ MHz, and f1, f2 to about 100 MHz, it is possible to set the resolution $\Delta t=|f1-f2|/(f1 \times f2)$ to about 100 ps (picosecond). Similarly, by setting f1, f2 to about 100 MHz, and the frequency difference $\Delta f$ to $\Delta f=100$ kHz, 10 kHz, and 1 kHz, it is possible to set the resolution $\Delta t$ to about 10 ps, 1 ps, and 0.1 ps, respectively. Further, the variation in oscillation frequency of each of the resonators XTAL1, XTAL2 is extremely small compared to the method of using the semiconductor element. Therefore, it is possible to realize both of the improvement of the resolution and the improvement of the accuracy.

Further, in the related art method of Document 4 described above, the time-to-digital conversion is realized using the quartz crystal oscillator. However, in this related art method, there is adopted a configuration of sequentially delaying the start timing of the time measurement from the timing of the synchronization point at which the edges of the first and second clock pulses match each other. Further, each time measurement is performed from the timing of the synchronization point at which the edges of the first and second clock pulses match each other, and the time measurement is required to be repeated a number of times. Therefore, there is a problem that the conversion time of the time-to-digital conversion becomes extremely long.

In contrast, in the repeating method of the present embodiment, the signal STA is generated a plurality of times in the measurement period TS to perform the phase comparison a plurality of times to thereby realize the time-to-digital conversion. Therefore, the time-to-digital conversion can dramatically be speeded up compared to the related art method.

7. Updating Method of Clock Cycle Designation Value

Then, as the time-to-digital conversion method according to the present embodiment, a method of realizing the time-to-digital conversion by the update of the clock cycle designation value (clock cycle designation information in a broad sense) will be described.

Figure 18:
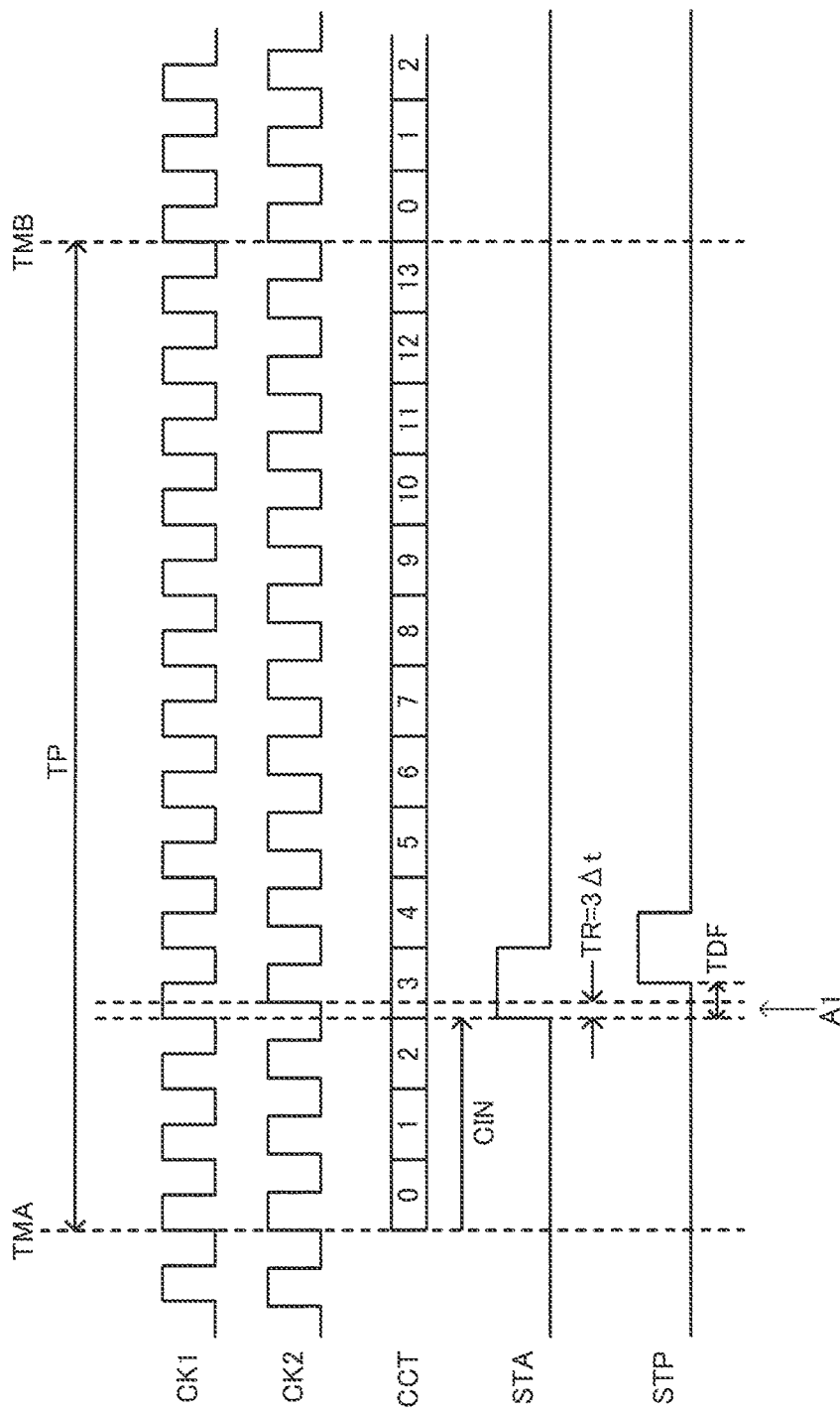
FIG. 18 is a signal waveform chart for explaining an updating method of the clock cycle designation value.
Figure 19:
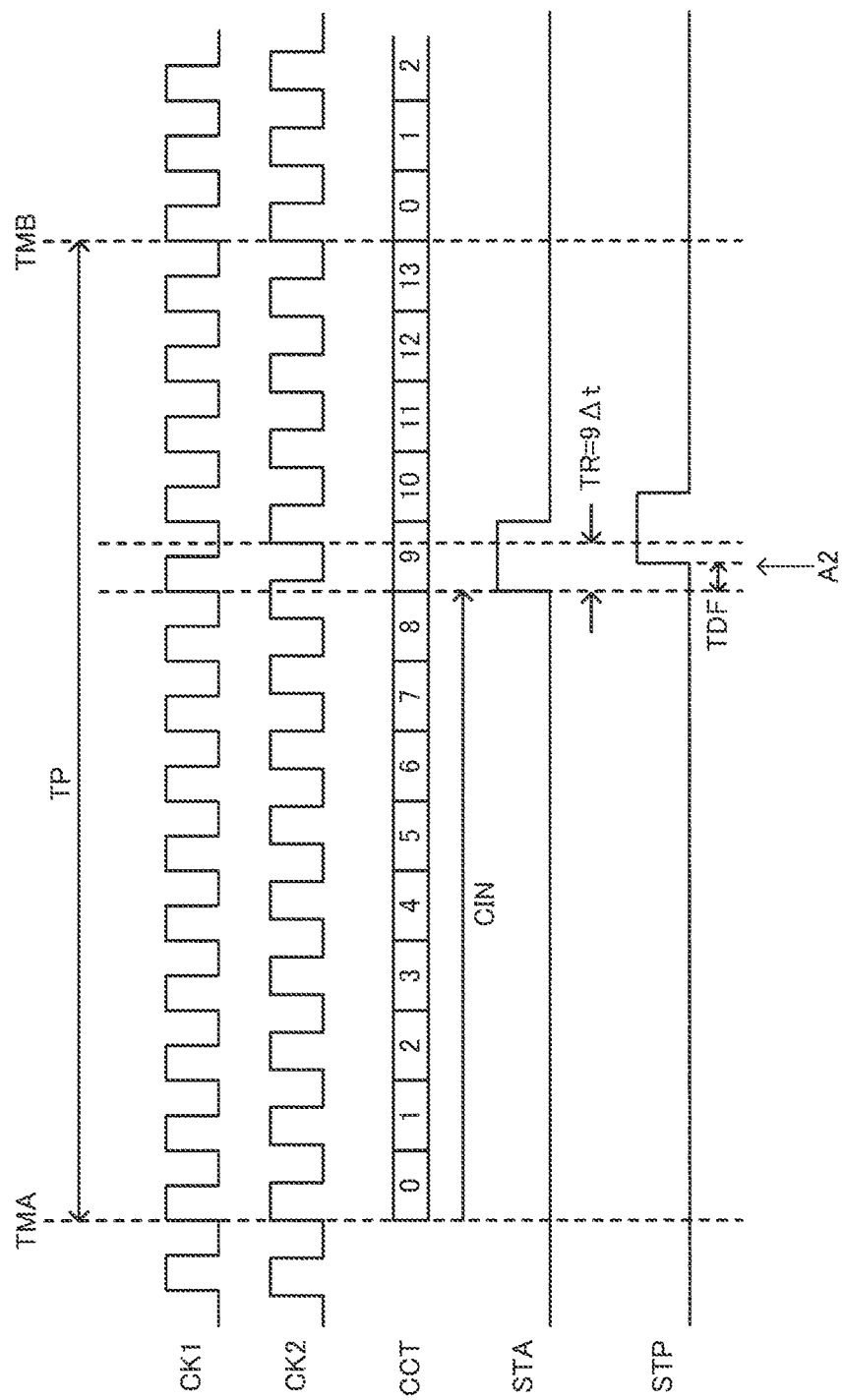
FIG. 19 is a signal waveform chart for explaining an updating method of the clock cycle designation value.
Figure 20:
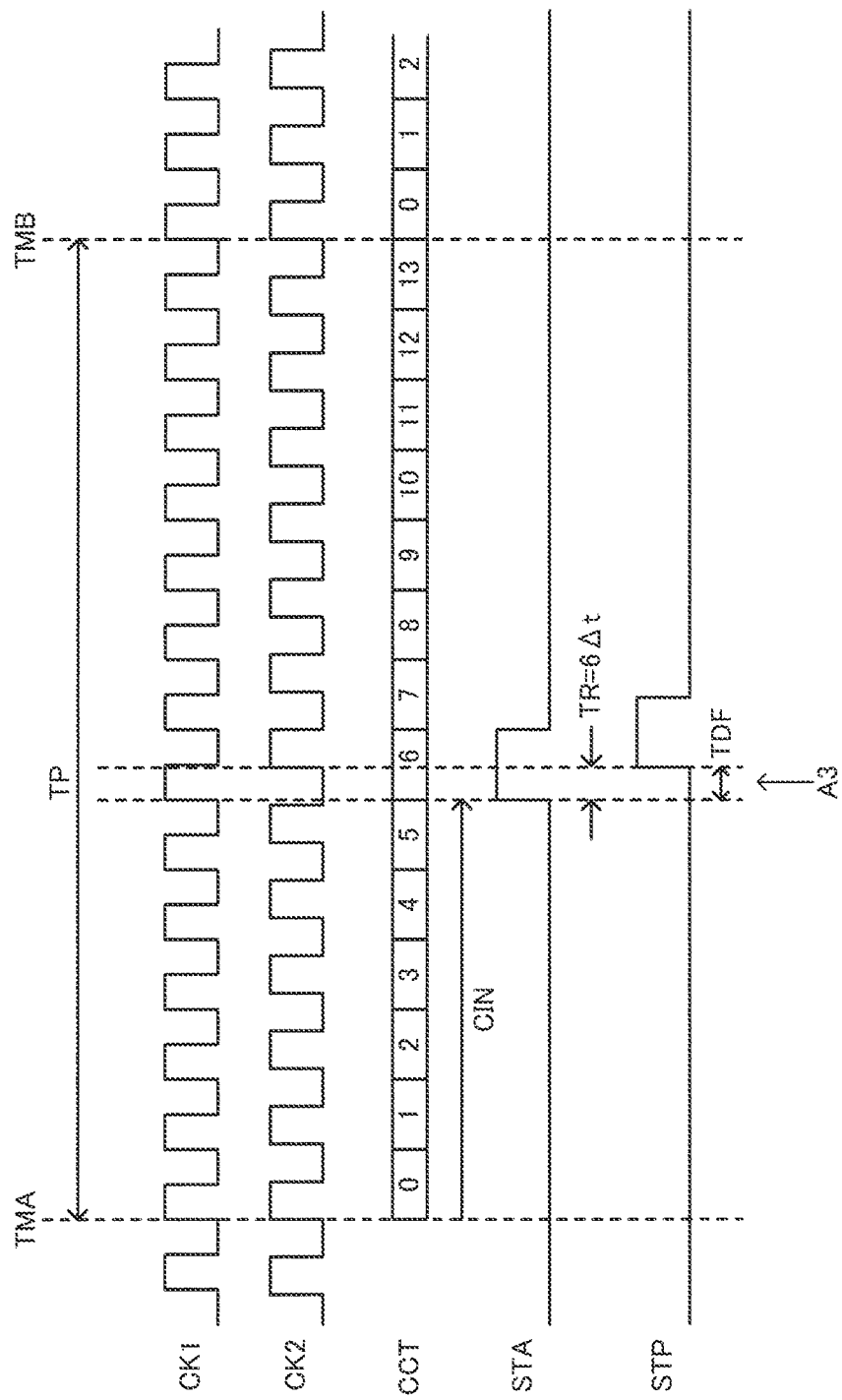
FIG. 20 is a signal waveform chart for explaining an updating method of the clock cycle designation value.

FIG. 18 through FIG. 20 are signal waveform charts for explaining the updating method of the clock cycle designation value (hereinafter arbitrarily described simply as an updating method). The reference symbol CIN denotes the clock cycle designation information. The description will hereinafter be presented assuming that CIN is the clock cycle designation value represented by the clock cycle designation information.

The reference symbols TMA, TMB are each the phase synchronization timing. In FIG. 18 through FIG. 20, the phase synchronization timings TMA, TMB are each the timing at which the transition timings (the rising edges) of the clock signals CK1, CK2 coincide with each other. It should be noted that the updating method of the present embodiment is not limited to the above, but the phase synchronization timings TMA, TMB each can also be the timing at which the anteroposterior relationship in phase between the clock signals CK1, CK2 is reversed. The timing at which the anteroposterior relationship in the phase is reversed is the timing at which the state in which one of the clock signals leads in phase over the other is switched to the state in which the one of the clock signals lags in phase behind the other.

The updating period TP is a period between the phase synchronization timings TMA, TMB. In the updating method of the present embodiment, the update of the clock cycle designation value is performed, for example, once in the updating period TP. It should be noted that in FIG. 18 through FIG. 20, there is shown the case in which the number of clock pulses of the clock signal CK1 in the updating period TP is 14 for the sake of simplification of the explanation. However, in reality, in order to set the high resolution, the number of clock pulses in the updating period TP is set to an extremely large number such as 1,000 or more (or 5,000 or more).

In the updating period TP (a first updating period) shown in FIG. 18, the clock cycle designation value is set to CIN=3. Therefore, the transition of the signal level of the signal STA is made in the clock cycle (CCT=3) designated by CIN=3. As described above, in the updating method of the present embodiment, the transition of the signal level of the signal STA is made in the clock cycle of the clock signal CK1 designated based on the clock cycle designation value CIN (the clock cycle designation information). Further, as described with reference to FIG. 3 and FIG. 4, the transition of the signal level of the signal STP is made in accordance with the signal STA, and the time difference in transition timing between the signals STA, STP is set to TDF.

In contrast, in the clock cycle (CCT=3) designated by CIN=3, the inter-clock time difference as the time difference in transition timing between the clock signals CK1, CK2 is set to TR=CIN×Δt=3×Δt as described with reference to FIG. 2.

In this case, in the updating method according to the present embodiment, the phase comparison between the signal STP and the clock signal CK2 is performed as indicated by the arrow A1 shown in FIG. 18. The phase comparison can be realized by sampling, for example, one of the signal STP and the clock signal CK2 with the other thereof.

Further, at the arrow A1 shown in FIG. 18, the phase comparison result, which is the result obtained by sampling the signal STP with the clock signal CK2, is in the L level. Due to the result of the phase comparison, it is determined that the signal STP lags in phase behind the clock signal CK2. In other words, at the arrow A1 shown in FIG. 18, TDF>TR=3×Δt is true, and the time difference TDF in transition timing between the signals STA, STP is longer than the inter-clock time difference TR=3×Δt between the clock signals CK1, CK2. In this case, there is performed the update of increasing the clock cycle designation value CIN.

In the updating period TP (a second updating period) shown in FIG. 19, the clock cycle designation value is set to CIN=9. For example, in the previous updating period TP shown in FIG. 18, by performing the update of increasing the clock cycle designation value from CIN=3 as described above, the clock cycle designation value is updated to CIN=9. Therefore, the transition of the signal level of the signal STA is made in the clock cycle (CCT=9) designated by CIN=9. Further, the transition of the signal level of the signal STP is made in accordance with the signal STA, and the time difference in transition timing between the signals STA, STP is set to TDF.

In contrast, in the clock cycle (CCT=9) designated by CIN=9, the inter-clock time difference between the clock signals CK1, CK2 is set to TR=CIN×Δt=9×Δt.

Further, in the updating method according to the present embodiment, the phase comparison between the signal STP and the clock signal CK2 is performed as indicated by the arrow A2 shown in FIG. 19. In this case, since the phase comparison result as the result obtained by sampling the signal STP with the clock signal CK2 is in the H level, there is determined that the signal STP leads in phase over the clock signal CK2. In other words, at the arrow A2 shown in FIG. 19, TDF<TR=9×Δt is true, and the time difference TDF is set shorter than the inter-clock time difference TR=9×Δt. In this case, there is performed the update of decreasing the clock cycle designation value CIN.

In the updating period TP (a third updating period) shown in FIG. 20, the clock cycle designation value is set to CIN=6. For example, in the previous updating period TP shown in FIG. 19, by performing the update of decreasing the clock cycle designation value from CIN=9 as described above, the clock cycle designation value is updated to CIN=6. Therefore, the transition of the signal level of the signal STA is made in the clock cycle (CCT=6) designated by CIN=6. Further, the transition of the signal level of the signal STP is made in accordance with the signal STA, and the time difference in transition timing between the signals STA, STP is set to TDF.

In contrast, in the clock cycle (CCT=6) designated by CIN=6, the inter-clock time difference between the clock signals CK1, CK2 is set to TR=CIN×Δt=6×Δt.

Further, in the updating method according to the present embodiment, the phase comparison between the signal STP and the clock signal CK2 is performed as indicated by the arrow A3 shown in FIG. 20. In this case, at the arrow A3 shown in FIG. 20, the signal STP and the clock signal CK2 coincide (roughly coincide) in transition timing (the phase) with each other. In other words, at the arrow A3 shown in FIG. 20, TDF=TR=6×Δt is true. Therefore, in this case, as the digital value obtained by converting the time difference TDF between the signals SAT, STP, the digital value corresponding to DQ=TR=6×Δt is output as the conclusive result.

It should be noted that although in FIG. 18 through FIG. 20, the increment and the decrement of the clock cycle designation value CIN between the updating periods are set to a value larger than 1, in reality, as in the case of the Δ-sigma type A/D conversion, the increment and the decrement of the clock cycle designation value CIN can be set to a small value GK equal to or smaller than 1. The value GK is a gain coefficient, and is a value fulfilling GK≤1.

For example, although in FIG. 18 and FIG. 19, the clock cycle designation value CIN is increased from 3 to 9, in reality, there is performed the update of increasing the clock cycle designation value CIN as much as the given value GK every updating period, for example. For example, in the case of setting the gain coefficient fulfilling GK≤1 as GK, there is performed the update of adding GK to the clock cycle designation value CIN. For example, in the case of GK=0.1, in the case in which, for example, the update of adding GK is continuously performed 10 times, the clock cycle designation value CIN is incremented as much as 1, as a result.

Further, although in FIG. 19 and FIG. 20, the clock cycle designation value CIN is decreased from 9 to 6, in reality, there is performed the update of decreasing the clock cycle designation value CIN as much as the given value GK every updating period, for example. For example, there is performed the update of subtracting GK from the clock cycle designation value CIN. For example, in the case of GK=0.1, in the case in which, for example, the update of subtracting GK is performed continuously 10 times, the clock cycle designation value CIN is decremented as much as 1, as a result.

Further, it is assumed that after the signal STP and the clock signal CK2 roughly coincide in transition timing with each other at the arrow A3 shown in FIG. 20, the clock cycle designation value CIN continues to be updated, and varies in such a manner as 6, 7, 6, 7, . . . . In this case, the digital value DQ to be output as the conclusive result can be set to a value (e.g., 6.5×Δt) between 6×Δt and 7×Δt. As described above, according to the updating method of the present embodiment, it is also possible to make the effective resolution finer as in the A-sigma type A/D conversion.

As described hereinabove, in the updating method of the present embodiment, the phase comparison between the signal STP and the clock signal CK2 is performed, wherein the transition of the signal level of the signal STP is made in accordance with the signal STA, and the clock cycle designation value CIN for making the transition of the signal level of the signal STA is updated based on the result of the phase comparison.

Specifically, the signal level of the signal STA is varied in the clock cycle designated by the clock cycle designation value CIN. For example, in FIG. 18, the transition of the signal level of the signal STA is made in the clock cycle designated by CIN=3. In FIG. 19, the transition of the signal level of the signal STA is made in the clock cycle designated by CIN=9. The same applies to FIG. 20.

Then, when the transition of the signal level of the signal STP is made in accordance with the signal STA, the phase comparison between the signal STP and the clock signal CK2 is performed, and then, the clock cycle designation value CIN is updated based on the phase comparison result. For example, in FIG. 18, since there is obtained the phase comparison result that the signal STA lags in phase behind the clock signal CK2, the clock cycle designation value CIN is updated from CIN=3 in FIG. 18 to CIN=9 in FIG. 19. In FIG. 19, since there is obtained the phase comparison result that the signal STA leads in phase over the clock signal CK2, the clock cycle designation value CIN is updated from CIN=9 in FIG. 19 to CIN=6 in FIG. 20. The conclusive value of the clock cycle designation value CIN updated in such a manner is output as the digital value DQ of the time difference TDF between the signals STA, STP.

Further, in the updating method of the present embodiment, the clock cycle designation value CIN continues to be updated in each of the updating periods. Further, there is adopted the configuration in which the clock cycle designation value CIN thus updated is fed back. Therefore, even in the case in which the time or the physical quantity to be the measurement object varies dynamically, it is possible to realize the time-to-digital conversion following the dynamic variation. For example, as indicated by the arrow A3 shown in FIG. 20, even in the case in which the clock cycle designation value CIN corresponding to the time (the time difference TDF) as the measurement object is approached, and then the time varies dynamically, it is possible to deal with such a dynamic variation by sequentially updating the clock cycle designation value CIN accordingly.

Further, in the updating method of the present embodiment, in the case of reducing the error component due to the discrepancy in transition timing between the clock signals CK1, CK2, it is desirable for the time-to-digital conversion circuit 20 to perform the process of converting the time difference into the digital value DQ based on the clock cycle designation value and the clock count information of the clock signal CK1 or the clock signal CK2 in the updating period of the clock cycle designation value. For example, by performing the update of the clock cycle designation value CIN based on the phase comparison result between the signal STP and the clock signal CK2, and the clock count information, the digital value DQ is obtained.

Therefore, in the updating method of the present embodiment, even if the transition timings of the clock signals CK1, CK2 fail to exactly coincide with each other at the phase synchronization timing, the time-to-digital conversion can be realized. For example, in the updating method of the present embodiment, it is sufficient for the phase synchronization timings TMA, TMB to be the timing at which the anteroposterior relationship in phase between the clock signals CK1, CK2 is reversed, and it is not required for the transition timings of the clock signals CK1, CK2 to completely coincide with each other. Therefore, in the present embodiment, it is also possible to adopt a practical modification of eliminating the PLL circuits 120, 130.

For example, in order to make the transition timings of the clock signals CK1, CK2 exactly coincide with each other at the phase synchronization timing, it is necessary to fulfill the relationship of $N/f1=M/f2$. Here, N, M are numbers of clock pulses of the clock signals CK1, CK2 in the updating period, respectively, and are each an integer equal to or greater than 2. However, in some cases, it is actually difficult to set the clock frequencies f1, f2 due to the resonators XTAL1, XTAL2 shown in FIG. 1 to the frequencies exactly fulfilling the relationship of $N/f1=M/f2$. Further, in the case in which the relationship of $N/f1=M/f2$ is not fulfilled, if the PLL circuits 120, 130 are not provided, a shift is caused between the transition timings of the clock signals CK1, CK2 at the phase synchronization timings TMA, TMB, and there is a possibility that the shift turns to the conversion error.

Therefore, in the updating method of the present embodiment, the number of clock pulses N in each of the updating periods is measured. Due to the shift existing between the transition timings of the clock signals CK1, CK2 at the phase synchronization timings TMA, TMB, the number of clock pulses N fails to be a constant value at all times, but varies between the updating periods. The time-to-digital conversion circuit 20 performs the update of the clock cycle designation value CIN based on the number of clocks N varying in such a manner, and the phase comparison result between the signal STP and the clock signal CK2. By adopting this configuration, the conversion error caused by the shift between the transition timings of the clock signals CK1, CK2 at the phase synchronization timings TMA, TMB can be reduced.

8. Binary Search Method

Then, a binary search method will be described as the time-to-digital conversion method of the present embodiment.

Figure 21:
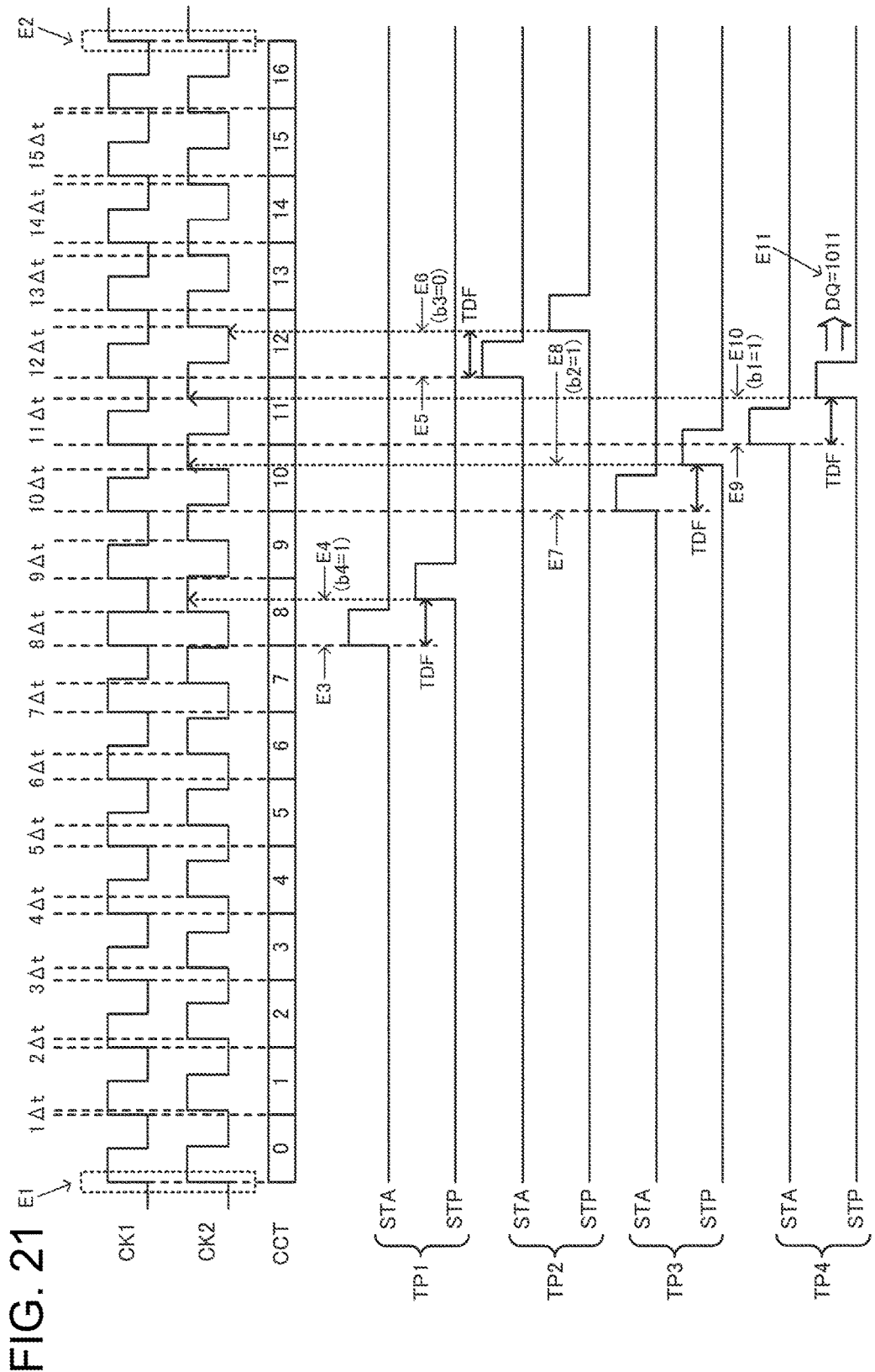
FIG. 21 is a signal waveform chart for explaining a binary search method.

FIG. 21 is a signal waveform chart for explaining the binary searching method. In FIG. 21, the digital value corresponding to the time difference in transition timing between the signal STA and the signal STP is obtained using the binary search method with the resolution corresponding to the frequency difference between the clock frequencies f1, f2. Specifically, the update of the clock cycle designation value CIN based on the phase comparison result between the signal STP and the clock signal CK2 is achieved by the binary search.

The binary search (dichotomizing search, a dual-partitioning method) is a method of sequentially obtaining the conclusive digital value while narrowing the search range by dividing (dividing into two parts) the search range one after another. For example, the digital value DQ obtained by converting the time difference is assumed to be 4-bit data, and the bits of the 4-bit data are defined as b4, b3, b2, and b1, respectively. The bit b4 is the MSB, and the bit b1 is the LSB. In FIG. 21, the bits b4, b3, b2, and b1 of the digital value DQ are obtained by the binary search. For example, due to a similar method to the successive approximation A/D conversion, the bits b4, b3, b2, and b1 of the digital value DQ are obtained in series.

For example, in FIG. 21, the clock frequencies of the clock signals CK1, CK2 are set to, for example, f1=100 MHz (the period is 10 ns), and f2=94.12 MHz (the period is 10.625 ns), and the resolution Δt is set to Δt=0.625 ns. Further, E1, E2 in FIG. 21 denote the phase synchronization timings at which the clock signals CK1, CK2 coincide, for example, in transition timing with each other. Further, the clock cycle designation value CIN is set to, for example, CIN=8 as an initial value. The initial value of CIN=8 corresponds to a value, for example, around the middle of the first search range.

If CIN=8 is set as described above, in the first updating period TP1 (a first updating period), as indicated by the arrow E3 in FIG. 21, the transition of the signal level of the signal STA is made in the case in which the clock cycle value reaches CCT=8. When the transition of the signal level of the signal STP is made in accordance with the signal STA, the phase comparison between the signal STP and the clock signal CK2 is performed. For example, the phase comparison of sampling the clock signal CK2 with the signal STP is performed, the H level of the clock signal CK2 is sampled as indicated by the arrow E4, and the H level is set as the phase comparison result. In the case in which the phase comparison result is the H level as described above, the logic level of the bit b4 as the MSB of the digital value DQ is determined as b4=1.

Since b4=1 is obtained in such a manner, the search range of the binary search is narrowed, and it is determined that the CIN corresponding to the conclusive digital value DQ exists within the search range of, for example, 8 through 15. Then, the clock cycle designation value is updated to, for example, CIN=12 so as to be set to the value (e.g., a value around the middle thereof) within the search range.

If the update to CIN=12 is performed as described above, in the subsequent updating period TP2 (a second updating period), as indicated by the arrow E5, the transition of the signal level of the signal STA is made in the case in which the clock cycle value reaches CCT=12. Then, the phase comparison between the signal STP and the clock signal CK2 is performed, and since the L level of the clock signal CK2 is sampled as indicated by, for example, the arrow E6, the L level is set as the phase comparison result. In the case in which the phase comparison result is the L level as described above, the logic level of the next bit b3 of the digital value DQ is determined as b3=0.

Since b4=1 and b3=0 are obtained in such a manner, the search range of the binary search is narrowed, and it is determined that the CIN corresponding to the conclusive digital value DQ exists within the search range of, for example, 8 through 11. Then, the clock cycle designation value is updated to, for example, CIN=10 so as to be set to the value (e.g., a value around the middle thereof) within the search range.

If the update to CIN=10 is performed as described above, in the subsequent updating period TP3 (a third updating period), as indicated by the arrow E7, the transition of the signal level of the signal STA is made in the case in which the clock cycle value reaches CCT=10. Then, the phase comparison between the signal STP and the clock signal CK2 is performed, and since the H level of the clock signal CK2 is sampled as indicated by, for example, the arrow E8, the H level is set as the phase comparison result. In the case in which the phase comparison result is the H level as described above, the logic level of the next bit b2 of the digital value DQ is determined as b2=1.

Lastly, the update to CIN=11 is performed, and in the subsequent updating period TP4 (a fourth updating period), as indicated by the arrow E9, the transition of the signal level of the signal STA is made in the case in which the clock cycle value reaches CCT=11. Then, the phase comparison between the signal STP and the clock signal CK2 is performed, and since the H level of the clock signal CK2 is sampled as indicated by, for example, the arrow E10, the H level is set as the phase comparison result. In the case in which the phase comparison result is the H level as described above, the bit b1 as the LSB of the digital value DQ is set to b1=1. Then, as indicated by the arrow E11, DQ=1011 (binary number) is output as the output code as the conclusive digital value.

By using the method of such binary search, it becomes possible to quickly obtain the digital value DQ corresponding to the time difference in transition timing between the signals STA, STP. For example, in the related art method of Document 4 described above, in the case of FIG. 21, the time measurement up to, for example, 15 times is necessary for obtaining the conclusive digital value DQ. In contrast, according to the method of the present embodiment, as shown in FIG. 21, the conclusive digital value DQ can be obtained with, for example, four times of updating periods, and thus, the speeding-up of the time-to-digital conversion can be achieved.

In particular, in the case in which the resolution Δt is made finer, and the number of bits L of the digital value DQ becomes large, the related art method requires to perform the time measurement, for example, about $2^L$ times, and thus, the conversion time becomes extremely long. In contrast, according to the method of the present embodiment, the conclusive digital value DQ can be obtained with, for example, L times of updating periods, and thus, the dramatic speeding-up of the time-to-digital conversion can be achieved compared to the related art method.

It should be noted that after obtaining the higher bit side of the digital value DQ using the binary search method shown in FIG. 21, it is possible to obtain the lower bit side (e.g., lower bits including the LSB, or the LSB as the lower bit) using the updating method explained with reference to, for example, FIG. 18 through FIG. 20. For example, in FIG. 21, the clock cycle designation value CIN is updated so as to become a value within the search range while sequentially narrowing the search range (successive approximation range) as in the successive approximation type A/D conversion. In contrast, in the updating method shown in FIG. 18 through FIG. 20, the update of increasing or decreasing the clock cycle designation value CIN by ±GK based on the phase comparison result as in the case of the A-sigma type A/D conversion. The value GK is a gain coefficient, and fulfills GK≤1. Specifically, in the case of the phase comparison result that the signal STP lags in phase behind the clock signal CK2, the update (digital arithmetic processing) of increasing the clock cycle designation value CIN by +GK is performed. In contrast, in the case of the phase comparison result that the signal STP leads in phase over the clock signal CK2, the update (digital arithmetic processing) of decreasing the clock cycle designation value CIN by GK is performed. By combining the two methods with each other as described above, it becomes possible to achieve both of the speeding-up and the increase in resolution of the time-to-digital conversion.

9. Physical Quantity Measurement Device, Electronic Apparatus, and Vehicle

Figure 22:
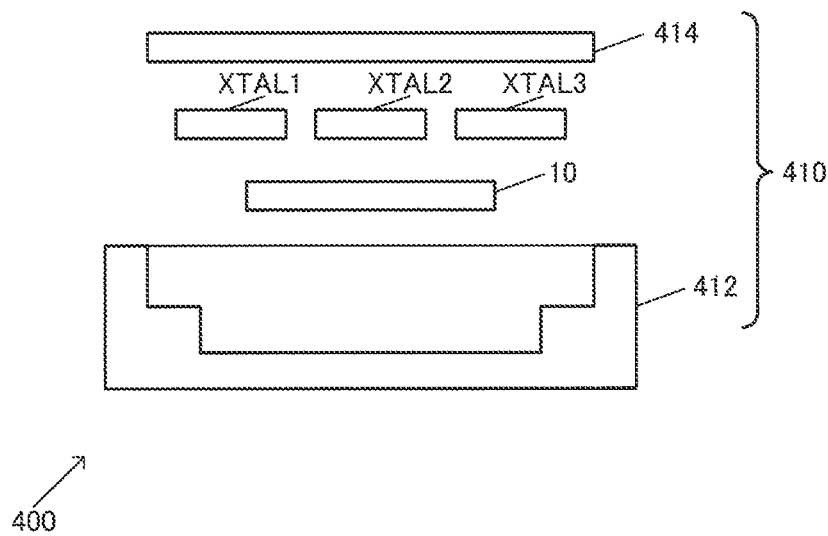
FIG. 22 is a diagram showing a configuration example of a physical quantity measurement device.

FIG. 22 shows a configuration example of the physical quantity measurement device 400 according to the present embodiment. The physical quantity measurement device 400 includes the circuit device 10 according to the present embodiment, the resonator XTAL1 (a first resonator, a first resonator element) for generating the clock signal CK1, and the resonator XTAL2 (a second resonator, a second resonator element) for generating the clock signal CK2. Further, it is also possible to include the resonator XTAL3 (a third resonator, a third resonator element) for generating the reference clock signal CKR. Further, it is possible for the physical quantity measurement device 400 to include a package 410 for housing the circuit device 10, and the resonators XTAL1, XTAL2, and XTAL3. The package 410 is formed of, for example, a base section 412 and a lid section 414. The base section 412 is a member made of an insulating material such as ceramic, and having, for example, a box-like shape, and the lid section 414 is a member to be bonded to the base section 412, and having, for example, a plate-like shape. On the bottom surface, for example, of the base section 412, there are disposed external connection terminals (external electrodes) to be connected to external equipment. In an internal space (a cavity) formed by the base section 412 and the lid section 414, there are housed the circuit device 10 and the resonators XTAL1, XTAL2, and XTAL3. Further, by sealing the internal space with the lid section 414, the circuit device 10 and the resonators XTAL1, XTAL2, and XTAL3 are airtightly encapsulated in the package 410.

The circuit device 10 and the resonators XTAL1, XTAL2, and XTAL3 are installed in the package 410. Further, terminals of the resonators XTAL1, XTAL2, and XTAL3 and terminals (pads) of the circuit device 10 (IC) are electrically connected respectively to each other with internal interconnections of the package 410. The circuit device 10 is provided with the oscillation circuits 101, 102, and 103 for oscillating the resonators XTAL1, XTAL2, and XTAL3, and by oscillating the resonators XTAL1, XTAL2, and XTAL3 using these oscillation circuits 101, 102, and 103, the clock signals CK1, CK2, and the reference clock signal CKR are generated.

For example, in the related art method of Document 4 described above, the first and second oscillation circuits are provided respectively to the first and second quartz crystal oscillators, and the circuit device does not incorporate the first and second oscillation circuits. Therefore, it is not possible to realize the phase synchronization between the first and second clock signals due to the PLL circuits 120, 130. Further, there is a disadvantage that it is not possible to perform the control process common to the first and second oscillation circuits in the circuit device.

It should be noted that a variety of practical modifications can be made as the configuration of the physical quantity measurement device 400. It is also possible for, for example, the base section 412 to have a plate-like shape, and for the lid section 414 to have a shape provided with a recess formed inside the lid section 414. Further, a variety of practical modifications can be made on the installation configuration and the wiring connection of the circuit device 10 and the resonators XTAL1, XTAL2, and XTAL3 in the package 410. Further, the resonators XTAL1, XTAL2, and XTAL3 are not required to be configured as completely separated parts, but can also be first and second oscillation areas provided to a single member. Further, it is also possible to provide the physical quantity measurement device 400 (the package 410) with four or more resonators. In this case, it is sufficient to provide four or more oscillation circuits corresponding respectively to the resonators to the circuit device 10.

Figure 23:
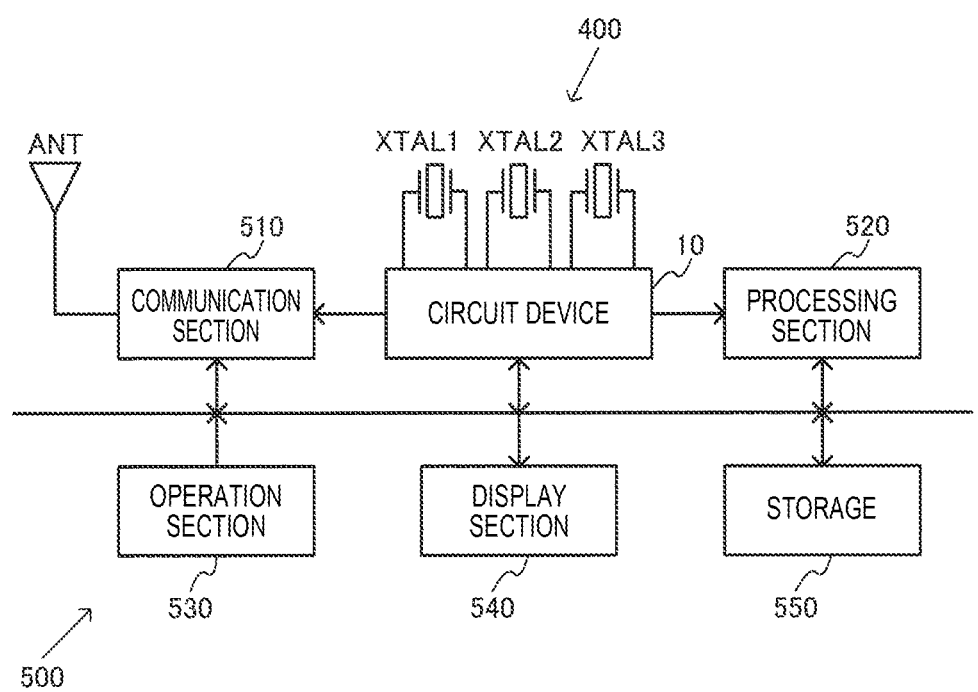
FIG. 23 is a diagram showing a configuration example of an electronic apparatus.

FIG. 23 shows a configuration example of an electronic apparatus 500 including the circuit device 10 according to the present embodiment. The electronic apparatus 500 includes the circuit device 10 according to the present embodiment, the resonators XTAL1, XTAL2, and XTAL3, and a processing section 520. Further, the electronic apparatus 500 can include a communication section 510, an operation section 530, a display section 540, a storage 550, and an antenna ANT. The circuit device 10 and the resonators XTAL1, XTAL2, and XTAL3 constitute the physical quantity measurement device 400. It should be noted that the configuration of the electronic apparatus 500 is not limited to the configuration shown in FIG. 23, but it is possible to adopt a variety of practical modifications such as elimination of some of the constituents or addition of other constituents.

As the electronic apparatus 500, there can be assumed a variety of apparatuses such as a measurement instrument for measuring a physical quantity such as a distance, time, flow speed, or a flow rate, a biological information measurement apparatus (e.g., a ultrasonic measurement device, a sphygmograph, and a blood-pressure measurement device), an in-car apparatus (e.g., equipment for automated driving), a network-related apparatus such as a base station, or a router, a wearable apparatus such as a head-mounted display device, or a timepiece related apparatus, a printer, a projection apparatus, a robot, a portable information terminal (e.g., a smartphone, a cellular phone, a portable video game player, a laptop PC, or a tablet PC), a content supply terminal for delivering contents, a video apparatus such as a digital camera or a video camera.

The communication section 510 (a wireless circuit) performs a process of receiving data externally via the antenna ANT and transmitting data to the outside. The processing section 520 performs a control process of the electronic apparatus 500, a variety of types of digital processing of the data transmitted or received via the communication section 510. Further, the processing section 520 performs a variety of processes using the physical quantity information measured by the physical quantity measurement device 400. The function of the processing section 520 can be realized by a processor such as a microcomputer.

The operation section 530 is for allowing the user to perform an input operation, and can be realized by operation buttons, a touch panel display, and so on. The display section 540 is for displaying a variety of types of information, and can be realized by a display using a liquid crystal, an organic EL, and so on. It should be noted that in the case of using the touch panel display as the operation section 530, it results that the touch panel display also functions as the operation section 530 and the display section 540. The storage 550 is for storing the data, and the function thereof can be realized by a semiconductor memory such as a RAM or a ROM, a hard disk drive (HDD), or the like.

Figure 24:
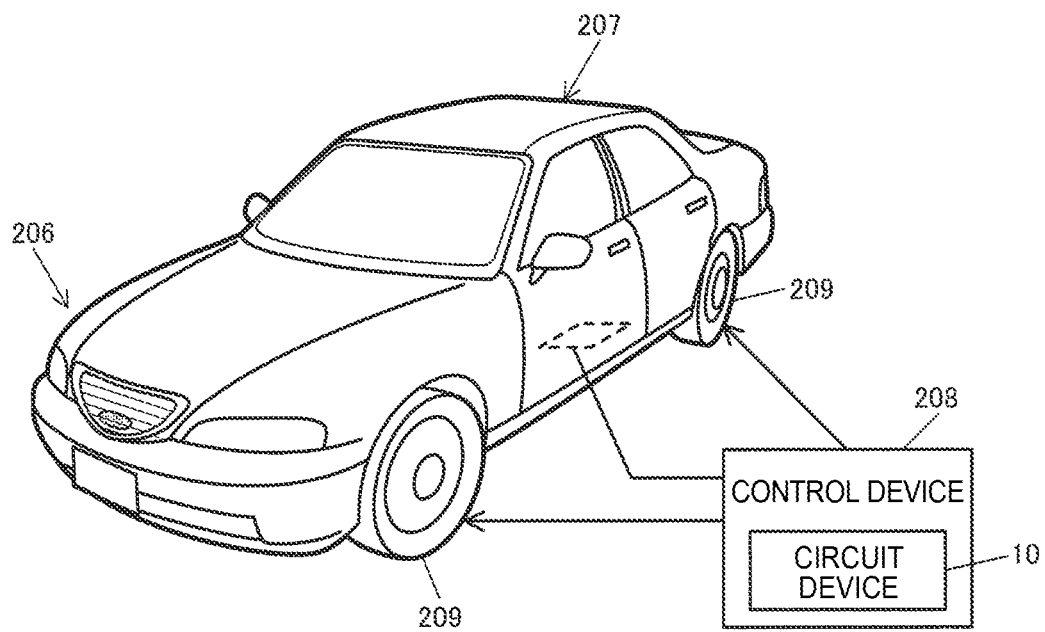
FIG. 24 is a diagram showing a configuration example of a vehicle.

FIG. 24 shows an example of a vehicle including the circuit device 10 according to the present embodiment. The circuit device 10 (the oscillator) according to the present embodiment can be incorporated in a variety of types of vehicles such as a car, an airplane, a motorbike, a bicycle, a robot, a ship, and a boat. The vehicle is equipment or an apparatus, which is provided with a drive mechanism such as an engine or an electric motor, a steering mechanism such as a steering wheel or a helm, and a variety of electronic apparatuses (in-car equipment), and moves on the ground, in the air, or on the sea. FIG. 24 schematically shows a car 206 as a specific example of the vehicle. The car 206 (the vehicle) incorporates a physical quantity measurement device (not shown) having the circuit device 10 according to the present embodiment and an resonator (not shown). The control device 208 performs a variety of control processes based on the physical quantity information measured by the physical quantity measurement device. For example, in the case in which the distance information of an object located in the periphery of the car 206 is measured as the physical quantity information, the control device 208 performs a variety of control processes for the automated driving using the distance information thus measured. The control device 208 controls the stiffness of the suspension in accordance with, for example, the attitude of a car body 207, and controls the brake of each of the wheels 209. It should be noted that the apparatus incorporating the circuit device 10 or the physical quantity measurement device according to the present embodiment is not limited to such a control device 208, but the circuit device or the physical quantity measurement device according to the present embodiment can be incorporated in a variety of apparatuses (in-car equipment) provided to a vehicle such as the car 206.

It should be noted that although the present embodiment is hereinabove described in detail, it should easily be understood by those skilled in the art that it is possible to make a variety of modifications not substantially departing from the novel matters and the advantage of the invention. Therefore, all of such modified examples should be included in the scope of the invention. For example, a term (e.g., clock cycle designation value, control voltage or PLL circuit) described at least once with a different term (e.g., clock cycle designation information, control signal or synchronizing circuit) having a broader sense or the same meaning in the specification or the accompanying drawings can be replaced with the different term in any part of the specification or the accompanying drawings. Further, all of the combinations of the present embodiment and the modified examples are also included in the scope of the invention. Further, the configurations and actions of the circuit device, the physical quantity measurement device, an electronic apparatus, and the vehicle, the configuration of the PLL circuit, the phase synchronization process, the oscillation process, the time-to-digital conversion process, the generation process of the first and second signals, the phase comparison process, and so on are not limited to those described as the present embodiment, but a variety of practical modifications can be made.

The entire disclosure of Japanese Patent Application No. 2017-030680, filed Feb. 22, 2017 is expressly incorporated by reference herein.

What is claimed is:

1. A circuit device comprising:
a first PLL circuit that receives a first clock signal having a first clock frequency generated by a first resonator and a reference clock signal, and performs phase synchronization between the first clock signal and the reference clock signal;
a second PLL circuit that receives a second clock signal generated by a second resonator and having a second clock frequency different from the first clock frequency and the reference clock signal, and performs phase synchronization between the second clock signal and the reference clock signal; and
a time-to-digital conversion circuit adapted to convert time into a digital value using the first clock signal and the second clock signal.

2. The circuit device according to claim 1, wherein the reference clock signal is a clock signal generated using a third resonator.

3. The circuit device according to claim 1, wherein the time-to-digital conversion circuit converts the time into the digital value with resolution corresponding to a frequency difference between the first clock frequency and the second clock frequency.

4. The circuit device according to claim 3, wherein defining the first clock frequency as f1 and the second clock frequency as f2, the time-to-digital conversion circuit converts the time into the digital value with the resolution Δt expressed as follows:

$$\Delta t = |f1-f2|/(f1 \times f2).$$

5. The circuit device according to claim 1, wherein in a case of defining the first clock frequency as f1, the second clock frequency as f2, and a clock frequency of the reference clock signal as fr,
the first PLL circuit performs the phase synchronization between the first clock signal and the reference clock signal so as to fulfill N1/f1=M1/fr (N1 and M1 are each no smaller than 2, and are different from each other), and
the second PLL circuit performs the phase synchronization between the second clock signal and the reference clock signal so as to fulfill N2/f2=M2/fr (N2 and M2 are each no smaller than 2, and are different from each other).

6. The circuit device according to claim 5, wherein N1, M1, N2, and M2 are set so that a relationship of |N1×M2−N2×M1|=1 is true.

7. The circuit device according to claim 5, wherein in a case of defining a resolution of the time-to-digital conversion as Δt, and N and M as N=N1×M2, M=N2×M1, the phase synchronization between the first clock signal and the second clock signal is performed by the first PLL circuit and the second PLL circuit so as to fulfill the following expression:

$$\Delta t = |N-M|/(N \times f2) = |N-M|/(M \times f1).$$

8. The circuit device according to claim 1, wherein the first PLL circuit includes a first phase detector adapted to perform phase comparison between one of the first clock signal and a signal based on the first clock signal, and one of the reference clock signal and a signal based on the reference clock signal, and
the second PLL circuit includes a second phase detector adapted to perform phase comparison between one of the second clock signal and a signal based on the second clock signal, and one of the reference clock signal and a signal based on the reference clock signal.

9. The circuit device according to claim 8, wherein the first PLL circuit includes
a first frequency divider circuit adapted to divide the frequency of the first clock signal to obtain a first frequency-divided clock signal, and output the first frequency-divided clock signal to the first phase detector as the signal based on the first clock signal, and
a second frequency divider circuit adapted to divide the frequency of the reference clock signal to obtain a second frequency-divided clock signal, and output the second frequency-divided clock signal to the first phase detector as the signal based on the reference clock signal, and
the second PLL circuit includes
a third frequency divider circuit adapted to divide the frequency of the second clock signal to obtain a third frequency-divided clock signal, and output the third frequency-divided clock signal to the second phase detector as the signal based on the second clock signal, and a fourth frequency divider circuit adapted to divide the frequency of the reference clock signal to obtain a fourth frequency-divided clock signal, and output the fourth frequency-divided clock signal to the second phase detector as the signal based on the reference clock signal.

10. The circuit device according to claim 9, wherein
in a case of defining the first clock frequency as f1, the second clock frequency as f2, and a frequency of the reference clock signal as fr,
the first frequency divider circuit divides the frequency of the first clock signal and the second frequency divider circuit divides the frequency of the reference clock signal so as to fulfill N1/f1=M1/fr (N1 and M1 are each no smaller than 2, and are different from each other), and
the third frequency divider circuit divides the frequency of the second clock signal and the fourth frequency divider circuit divides the frequency of the reference clock signal so as to fulfill N2/f2=M2/fr (N2 and M2 are each no smaller than 2, and are different from each other).

11. The circuit device according to claim 8 further comprising:
a first oscillation circuit controlled based on a phase comparison result of the first phase detector, and adapted to oscillate the first resonator to generate the first clock signal; and
a second oscillation circuit controlled based on a phase comparison result of the second phase detector, and adapted to oscillate the second resonator to generate the second clock signal.

12. The circuit device according to claim 11, further comprising:
a third oscillation circuit adapted to oscillate a third resonator to generate the reference clock signal.

13. The circuit device according to claim 1, wherein
the time-to-digital conversion circuit converts a time difference in transition timing between a first signal and a second signal into a digital value.

14. A physical quantity measurement device comprising:
the circuit device according to claim 1;
the first resonator adapted to generate the first clock signal; and
the second resonator adapted to generate the second clock signal.

15. A physical quantity measurement device comprising:
the circuit device according to claim 2;
the first resonator adapted to generate the first clock signal; and
the second resonator adapted to generate the second clock signal.

16. A physical quantity measurement device comprising:
the circuit device according to claim 3;
the first resonator adapted to generate the first clock signal; and
the second resonator adapted to generate the second clock signal.

17. An electronic apparatus comprising:
the circuit device according to claim 1.

18. An electronic apparatus comprising:
the circuit device according to claim 2.

19. A vehicle comprising:
the circuit device according to claim 1.

20. A vehicle comprising:
the circuit device according to claim 2.

* * * * *